(12) United States Patent
Kaplan et al.

(10) Patent No.: US 9,539,362 B2
(45) Date of Patent: Jan. 10, 2017

(54) METHOD FOR FORMING INORGANIC COATINGS

(75) Inventors: David L. Kaplan, Concord, MA (US); Chunmei Li, Stoneham, MA (US)

(73) Assignee: Trustees of Tufts College, Medford, MA (US)

(*) Notice: Subject to any disclaimer, the term of this patent is extended or adjusted under 35 U.S.C. 154(b) by 463 days.

(21) Appl. No.: 12/762,515

(22) Filed: Apr. 19, 2010

(65) Prior Publication Data

US 2010/0203226 A1    Aug. 12, 2010

Related U.S. Application Data

(60) Division of application No. 11/289,039, filed on Nov. 29, 2005, now Pat. No. 7,727,575, which is a continuation of application No. PCT/US2004/017661, filed on Jun. 7, 2004.

(60) Provisional application No. 60/476,547, filed on Jun. 6, 2003.

(51) Int. Cl.

| A61L 27/22 | (2006.01) |
| A61L 27/30 | (2006.01) |
| A61L 27/44 | (2006.01) |
| A61L 27/46 | (2006.01) |
| A61L 27/24 | (2006.01) |

(52) U.S. Cl.
CPC ............. *A61L 27/227* (2013.01); *A61L 27/24* (2013.01); *A61L 27/30* (2013.01); *A61L 27/446* (2013.01); *A61L 27/46* (2013.01); *Y10T 428/24999* (2015.04); *Y10T 428/2933* (2015.01); *Y10T 428/31768* (2015.04); *Y10T 442/10* (2015.04)

(58) Field of Classification Search
None
See application file for complete search history.

(56) References Cited

U.S. PATENT DOCUMENTS

| 1,989,005 A | 1/1935 | Fink et al. |
| 4,233,212 A | 11/1980 | Otoi et al. |
| 4,820,418 A | 4/1989 | Hirotsu et al. |
| 5,047,507 A | 9/1991 | Buchegger et al. |
| 5,290,494 A | 3/1994 | Coombes et al. |
| 5,606,019 A | 2/1997 | Cappello |
| 5,728,810 A | 3/1998 | Lewis et al. |
| 5,770,193 A | 6/1998 | Vacanti et al. |
| 5,776,193 A | 7/1998 | Kwan et al. |
| 5,994,099 A | 11/1999 | Lewis et al. |
| 6,110,590 A | 8/2000 | Zarkoob et al. |
| 6,123,819 A | 9/2000 | Peeters |
| 6,175,053 B1 | 1/2001 | Tsubouchi |
| 6,187,047 B1 | 2/2001 | Kwan et al. |
| 6,423,252 B1 | 7/2002 | Chun et al. |
| 6,592,623 B1 | 7/2003 | Bowlin et al. |
| 6,733,715 B2 * | 5/2004 | Hozumi et al. ............... 264/430 |
| 6,815,427 B2 | 11/2004 | Tsubouchi et al. |
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,473,731 B2 | 1/2009 | Furuzono et al. |
| 7,635,755 B2 | 12/2009 | Kaplan |
| 7,662,409 B2 | 2/2010 | Masters |
| 7,674,882 B2 | 3/2010 | Kaplan et al. |
| 7,727,575 B2 | 6/2010 | Kaplan |
| 7,842,780 B2 | 11/2010 | Kaplan |
| 7,960,509 B2 | 6/2011 | Kaplan |
| 8,071,722 B2 | 12/2011 | Kaplan et al. |
| 2002/0028243 A1 | 3/2002 | Masters |
| 2003/0007991 A1 | 1/2003 | Masters |
| 2003/0183978 A1 | 10/2003 | Asakura |
| 2003/0232071 A1 | 12/2003 | Gower et al. |
| 2004/0005363 A1 | 1/2004 | Tsukada et al. |
| 2004/0078077 A1* | 4/2004 | Binette et al. ............ 623/13.17 |
| 2004/0266992 A1 | 12/2004 | Migliaresi et al. |
| 2006/0159837 A1 | 7/2006 | Kaplan et al. |
| 2007/0212370 A1 | 9/2007 | Vepari et al. |
| 2008/0085272 A1 | 4/2008 | Kaplan et al. |
| 2008/0293919 A1 | 11/2008 | Huang et al. |
| 2009/0202614 A1 | 8/2009 | Kaplan et al. |
| 2009/0232963 A1 | 9/2009 | Murphy et al. |
| 2009/0234026 A1 | 9/2009 | Kaplan et al. |
| 2010/0028451 A1 | 2/2010 | Kaplan |
| 2010/0046902 A1 | 2/2010 | Georgakoudi et al. |

(Continued)

FOREIGN PATENT DOCUMENTS

| CA | 2405850 | 10/2002 |
| EP | 1440088 | 7/2004 |

(Continued)

OTHER PUBLICATIONS

Sun et al., Acrylic Polymer-Silk Fibroin Blend Fibers, Journal of Applied Polymer Science (1997), vol. 65, pp. 959-966.*
Liang et al., Improvements of the Physical Properties of Fibroin Membranes with Sodium Aginate, Journal of Applied Polymer Science (1992), vol. 45, p. 1937-1943.*
Bradt et al., Biomimetic Mineralization of Collagen by Combined Fibril Assembly and Calcium Phosphate Formation, Chem. Mater. (1999), vol. 11, pp. 2694-2701.*
Zhang et al., Hierarchical Self-Assembly of Nano-Fibrils in Mineralized Collagen, Chem. Mater. (2003), vol. 15, pp. 3221-3226.*

(Continued)

*Primary Examiner* — Abigail Fisher
*Assistant Examiner* — Frank Choi
(74) *Attorney, Agent, or Firm* — Brenda Herschbach Jarrell; Brian E. Reese; Choate, Hall & Stewart LLP

(57) ABSTRACT

The present invention is directed to a method for forming an inorganic coating on a protein template. The method comprises contacting the template with an anionic polymer interface followed by an inorganic material for a sufficient period of time to allow mineralization of the inorganic material thus forming an inorganic coating on the template. Preferably, the coating is aligned.

14 Claims, 11 Drawing Sheets

(56) References Cited

U.S. PATENT DOCUMENTS

| | | | |
|---|---|---|---|
| 2010/0055438 | A1 | 3/2010 | Kaplan et al. |
| 2010/0063404 | A1 | 3/2010 | Georgakoudi et al. |
| 2010/0065784 | A1 | 3/2010 | Georgadoudi et al. |
| 2010/0068740 | A1 | 3/2010 | Perry et al. |
| 2010/0070068 | A1 | 3/2010 | Georgakoudi et al. |
| 2010/0096763 | A1 | 4/2010 | Georgakoudi et al. |
| 2010/0120116 | A1 | 5/2010 | Kaplan |
| 2010/0178304 | A1 | 7/2010 | Kaplan et al. |
| 2010/0191328 | A1 | 7/2010 | Marchant et al. |
| 2010/0196447 | A1 | 8/2010 | Kaplan et al. |
| 2011/0046686 | A1 | 2/2011 | Kaplan et al. |
| 2011/0076384 | A1 | 3/2011 | Cannizzaro et al. |
| 2011/0135697 | A1 | 6/2011 | Omenetto et al. |
| 2011/0152214 | A1 | 6/2011 | Boison et al. |
| 2011/0171239 | A1 | 7/2011 | Kaplan et al. |
| 2012/0121820 | A1 | 5/2012 | Kaplan et al. |
| 2012/0123519 | A1 | 5/2012 | Lovett et al. |
| 2013/0177608 | A1 | 7/2013 | Kaplan et al. |

FOREIGN PATENT DOCUMENTS

| | | |
|---|---|---|
| GB | 1182153 | 2/1970 |
| JP | S58-038449 | 10/1980 |
| JP | 60-142259 | 7/1985 |
| JP | 60-259677 | 12/1985 |
| JP | 01118544 | 11/1989 |
| JP | 06-346314 | 12/1994 |
| JP | 08-295697 | 11/1996 |
| JP | 10-36676 | 2/1998 |
| JP | 2000-273264 | 11/2000 |
| JP | 2003192807 | 7/2003 |
| JP | 2004068161 | 3/2004 |
| WO | 97/14376 A1 | 4/1997 |
| WO | 99/01089 | 1/1999 |
| WO | 01/36531 | 5/2001 |
| WO | 01/56626 | 8/2001 |
| WO | 02/072931 | 9/2002 |
| WO | 03/022909 | 3/2003 |
| WO | 03/038033 | 5/2003 |
| WO | 03/071991 A1 | 9/2003 |
| WO | 04/000915 | 12/2003 |
| WO | 2004/041845 | 5/2004 |
| WO | 2005/123114 | 12/2005 |

OTHER PUBLICATIONS

Chiarini et al., Biomaterials, 24:789-799 (2003). "Silk fibroin/poly(carbonate)-urethane as a substrate for cell growth."
Demura et al., Biosensors, 4:361-372 (1989). "Immobilization of biocatalysts with bombyx mori silk fibroin by several kinds of physical treatment and its application to glucose sensors."
Kato et al., Supramolecular Science, 5:411-415 (1998). "Effects of macomolecules on the crystallization of CaCO3 the formation of organic/inorganic composites."
Kong et al., Biomaterials Laboratory, Department of Materials Science and Engineering, Tsinghua University, Jul. 15, 2004. "Silk fibroin regulated mineralization of hydroxyapatite nanocrystals."
Mann et al., Inorganic Elements in Biochemistry, 54:125-174 (1983). "Mineralization in biological systems."
Naka et al., Chemistry of Materials, 13:3245-3259 (2001). "Control of crystal nucleation and growth of calcium carbonate by synthetic substrates."
Asakura et al., Journal of Membrane Science, 59:39-52 (1991). "Porous membrane of Bombyx mori silk fibroin: structure characterization, physical properties and application to glucose oxidase immobilization."
Asakura et al., Macromolecules, 17:1075-1081 (1984). "NMR of silk fibroin 2. C NMR study of the chain dynamics and solution structure of Bombyx mori silk fibroin."
Asakura et al., Macromolecules, 18:1841-1845 (1985). "Conformational characterization of B. mori silk fibroin in the solid state by high-frequency 13C cross polarization-magic angel spinning NMR, X-ray diffraction and infrared spectroscopy."
Chen et al., J Appl Polymer Sci, 65:2257-2262 (1997). "pH sensitivity and ion sensitivity of hydrogels based on complex-forming chitosan/silk fibroin interpenetrating polymer network."
Chen et al., J Appl Polymer Sci, 73:975-980 (1999). "Separation of alcohol-water mixture by pervaporation through a novel natural polymer blend membrane-chitosan/silk fibroin blend membrane."
Chen et al., Proteins: Structure, Function, and Bioinformatics, 68:223-231 (2007). "Conformation transition kinetics of Bombyx mori silk protein."
Database WPI Week 198205, Derwent Publications Ltd., London, GB AN 1982-09092E & JP 56 166235 A Dec. 21, 1981. Abstract.
Demura et al., Biosensors, 361-372 (1989). "Immobilization of biocatalysts with Bombyx mori silk fibroin by several kinds of physical treatment and its application to glucose sensors."
Demura et al., J Membrane Science, 59:32-52 (1991). "Porous membrane of Bombyx mori silk fibroin: structure characterization, physical properties and application to glucose oxidase immobilzation."
Derwent Record, Abstract of JP 08295697 A2 "Production of aqueous solution of silk fibroin at high concentration." Nov. 12, 1996.
Doshi et al. J Electrostatics, 35:151-160 (1995). "Electrospinning process and applications of electrospun fibers."
Freddi et al., J Appl Polymer Sci, 56:1537-1545 (1995). "Silk fibroin/cellulose blend films: preparation, structure, and physical properties."
Hijirida et al., Biophysical Journal, 71:3442-3447 (1996). "13C NMR of Nephila clavipes marjor ampullate silk gland."
Hinman et al., TIBTECH, 18:374-379 (2000). "Synthetic spider silk: a modular fiber."
Huang et al., J Biomater Sci Polymer Edn, 12(9):979-993 (2001). "Engineered collagen-PEO nanofibers and fabrics."
Huang et al., Macromolecules, 33:2989-2997 (2000). "Generation of synthetic elastin-mimetic small diameter fibers and fiber networks."
Jin et al., Biomacromolecules, 3:1233-1239 (2002). "Electrospinning Bombyx mori silk with poly(ethylene oxide)."
Kweon et al., J Appl Polymer Sci, 80:1848-1853 (2001). "Preparation of semi-interpenetrating polymer networks composed of silk fibroin and poly(ethylene glycol) macromer."
Lazaris, Science, 295:472-476 (2002). "Spider silk fibers spun from soluble recombinant silk produced in mammalian cells."
Liang et al., J Appl Polymer Sci, 45:1937-1943 (1992). "Improvements of the physical properties of fibroin membranes with sodium alginate."
Megeed et al., Pharmaceutical Research, 19(7):954-959 (2002). "Controlled release of plasmid DNA from a genetically engineered silk-elastinlike hydrogel."
Petrini et al., Journal of Materials Science: Materials in Medicine, 12:849-853 (2001). "Silk fibroin-polyurethane scaffolds for tissue engineering."
Reneker et al., Nanotechnology, 7:216-223 (1996). "Nanometre diameter fibres of polymer, produced by electrospinning."
Sawyer et al., JAMA, 191(9):740-742 (1965). "Dextran therapy in thrombophlebitis." Abstract.
U.S. Appl. No. 60/906,509, filed Mar. 13, 2007 by Perry et al.
U.S. Appl. No. 61/224,618, filed Jul. 10, 2009 by Perry et al.
Wang et al., Langmuir, 21:11335-11341 (2005). "Biomaterial coatings by stepwise deposition of silk fibroin."
Yamada et al., Thin Solid Films, 440:208-216 (2003). "AFM observation of silk fibrion on mica substrates: morphologies reflecting the secondary structure."
Zhou et al., Chem Commun, 2518-2519 (2001). "Preparation of a novel core-shell nanostructured gold colloid-silk fibroin bioconjugate by the protein in situ redox technique at room temperature."
He et al, Silk I structure in Bombyx mori silk foams, Int'l J Biological Macromolecules, 24:187-195 (1999).
International Search Report for PCT/US2004/017661, 1 page. (Nov. 10, 2004).

(56) References Cited

OTHER PUBLICATIONS

Li, C. et al., Silk apatite composites from electrospun fibers, J. Mater. Res., 20(12):3374-84 (2005).
Wilson et al, Conformational Transitions in Model Silk Peptides, Biophysical Journal, 78:2690-2701 (2000).
Written Opinion for PCT/US2004/017661, 3 pages. (Nov. 10, 2004).

* cited by examiner

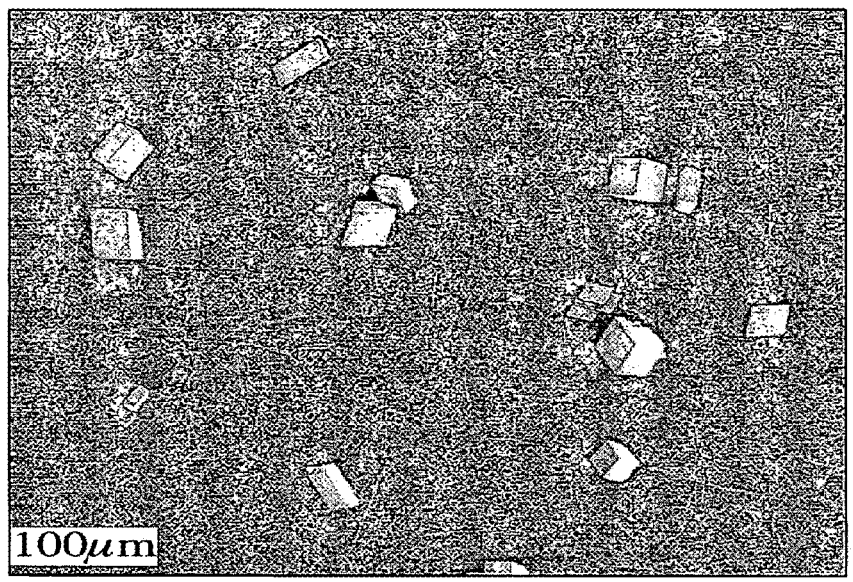
FIG. 5
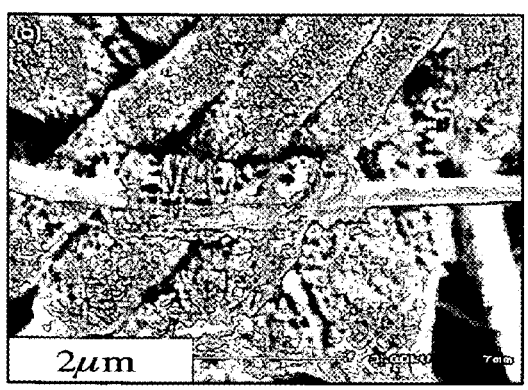 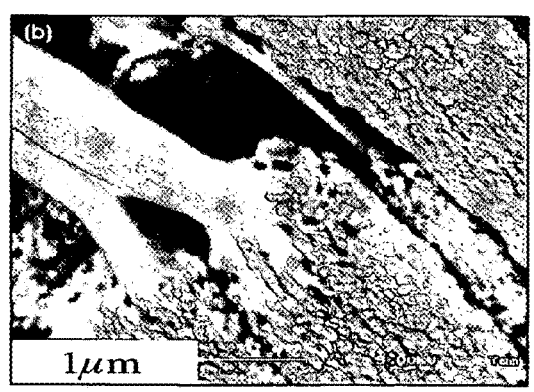
FIG. 6A  FIG. 6B

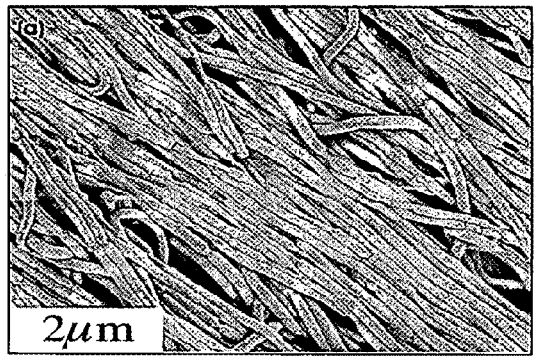 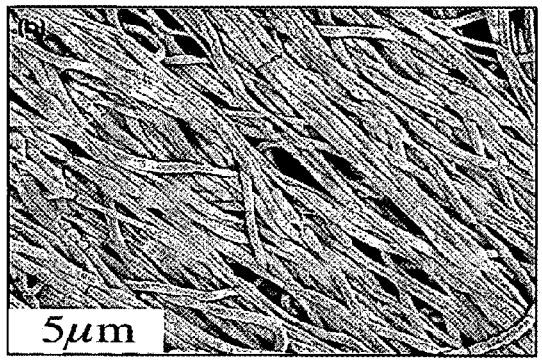
FIG. 10A  FIG. 10B
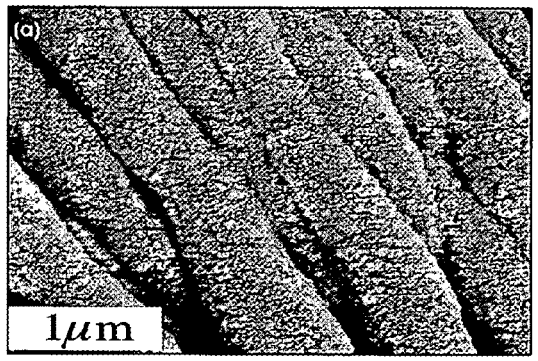 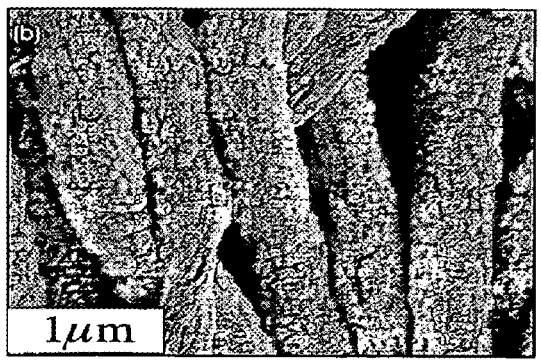
FIG. 11A  FIG. 11B

METHOD FOR FORMING INORGANIC COATINGS

CROSS REFERENCE TO RELATED APPLICATIONS

This application is a continuation application that claims benefit under 35 U.S.C. §120 of U.S. patent application Ser. No. 11/289,039, filed Nov. 29, 2005, now U.S. Pat. No. 7,727,575 B2, which is a continuation application that claims benefit under 35 U.S.C. §120 of International Application No. PCT/US04/17661, filed Jun. 7, 2004, designating the United States, which claims the benefit of priority under 35 U.S.C. 119(e) of U.S. Provisional Application No. 60/476,547, filed Jun. 6, 2003.

GOVERNMENT SUPPORT

This invention was made with government support under grant DE013405 awarded by the National Institutes of Health. The government has certain rights in the invention.

FIELD OF THE INVENTION

The present application is directed to a method of forming an inorganic coating on a protein template.

BACKGROUND OF THE INVENTION

Many biomedical procedures require the provision of healthy tissue to counteract the disease process or trauma being treated. This work is often hampered by the tremendous shortage of tissues available for transplantation and/or grafting. Tissue engineering may ultimately provide alternatives to whole organ or tissue transplantation.

In order to generate engineered tissues, various combinations of biomaterials and living cells are currently being investigated. Although attention is often focused on the cellular aspects of the engineering process, the design characteristics of the biomaterials also constitute a major challenge in this field.

In recent years, the ability to regenerate tissues and to control the properties of the regenerated tissue have been investigated by trying to specifically tune the mechanical or chemical properties of the biomaterial scaffold (Kim et al., 1997; Kohn et al. 1997). The majority of this work has involved the incorporation of chemical factors into the material during processing, or the tuning of mechanical properties by altering the constituents of the material.

The foregoing methods have been used in an attempt to utilize chemical or mechanical signaling to affect changes in the proliferation and/or differentiation of cells during tissue regeneration. Despite such efforts, there remains in the art a need for improved biomaterials, particularly those with a better capacity to support complex tissue growth in vitro (in cell culture) and in vivo (upon implantation).

SUMMARY OF THE INVENTION

The present invention provides a method for forming an aligned inorganic coating on a protein template. Preferably, the coating is aligned. The method comprises forming an anionic polymer interface on a protein template and contacting the interface with an inorganic material for a sufficient period of time to allow mineralization of the inorganic material, thus forming an inorganic coating on the template. Multiple cycles of mineralization can be performed.

Proteins useful for the protein template include structural proteins such as keratins, collagens and silks.

In one preferred embodiment the protein template comprises silk. The silk can be processed into various forms, for example, a fiber (e.g. electrospun), a film, a hydrogel, a foam, or a three-dimensional porous matrix.

In one embodiment, the anionic polymer interface is added to the template during formation of the template, for example, by mixing an anionic polymer with a silk fibroin solution prior to processing the silk into a fiber, foam, film, hydrogel, or porous matrix.

In another embodiment, the anionic polymer is adsorbed into or onto a preformed protein template.

The anionic polymer interface is preferably polyaspartic acid, polyacrylic acid, or alginic acid. Mixtures may also be used.

In one embodiment, the inorganic material used for mineralization is hydroxyapatite or silica.

In another embodiment, the inorganic material is an inorganic salt, such as calcium carbonate.

In one preferred embodiment, the template is pre-organized. For example, the template can be pre-organized into aligned fibers or two-dimensional surfaces by stretching.

In a further embodiment, a method for forming matrices, tubes, or sheets of inorganic material is provided. The method comprises (a) forming a protein template having an anionic polymer interface; contacting the template of step (a) with an inorganic material for a sufficient period of time to allow mineralization of the inorganic material, thus forming an inorganic coating on the template; and (c) removing the template after mineralization of the inorganic material. Multiple cycles of mineralization can be performed prior to removal of the template.

In another embodiment, therapeutic or biologically active agents are incorporated into the template with an inorganic coating, or are incorporated into the hollow matrices, tubes, or sheets of inorganic material. The therapeutic or biologically active agents can be mixed into the inorganic coating during formation of the inorganic coating. Alternatively, they can be added to the protein template during formation of the template, for example, by mixing with a silk fibroin solution prior to processing the silk into a fiber, foam, film, hydrogel, or porous matrix. Therapeutic or biologically active agents can also be incorporated into, or coated onto a preformed template.

In another embodiment, a method for forming an aligned inorganic coating on a protein template is provided that comprises: (a) contacting a protein template with poly-L-aspartic acid; and (b) contacting the template of step (a) with calcium carbonate for a sufficient period of time to allow mineralization of the calcium carbonate thus forming an inorganic coating on the template.

Products produced by the methods of the invention are also provided.

BRIEF DESCRIPTION OF THE DRAWINGS

FIG. 5 shows CaCO$_3$ minerals formed on aspartic acid soaking silk fiber.

FIGS. 6 a and 6b show fibers with pores after CaCO$_3$ mineralization on poly-Asp soaked silk matrix.

FIGS. 10 a and 10b show stretched silk matrix with no poly-Asp (a) and poly-Asp incorporated (b).

FIGS. 11 a and 11b show CaCO$_3$ minerals formed on aligned silk fibers on a poly-Asp soaked matrix (a) and on a poly-Asp incorporated matrix (b).

DETAILED DESCRIPTION OF THE INVENTION

The present invention provides a method for forming an inorganic coating on a protein template. Preferably, the coating is aligned. The method comprises contacting a protein template having an anionic polymer interface with an inorganic material for a sufficient period of time to allow mineralization of the inorganic material and thus forming an inorganic coating on the template. The interface can be contacted with the organic material multiple times.

Figure 2:
FIG. 2 shows $CaCO_3$ minerals formed on poly(aspartic acid) (poly-Asp) soaking silk fiber.
Figure 3:
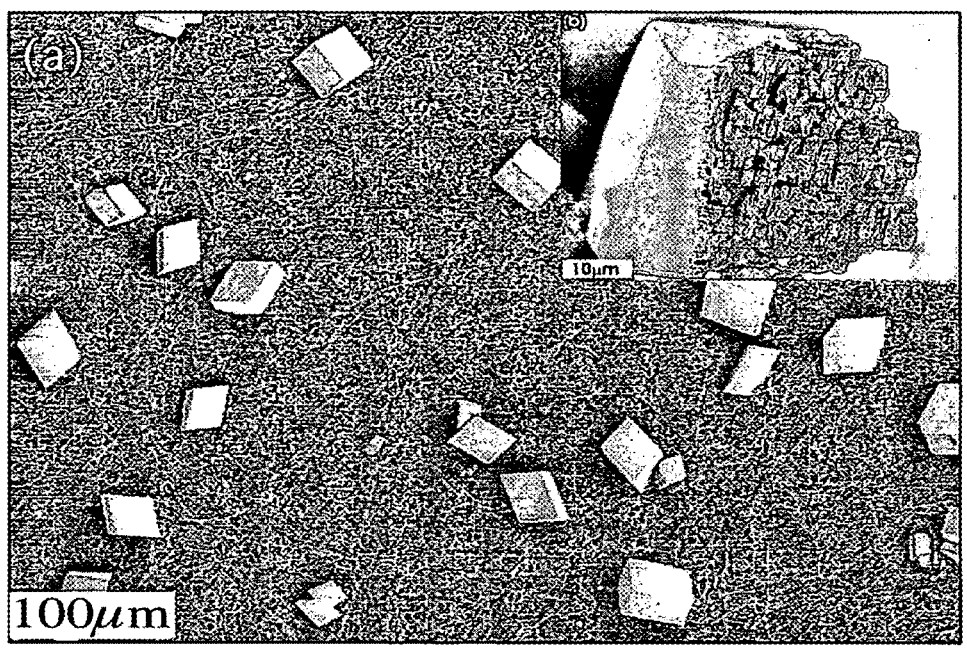
FIG. 3a shows $CaCO_3$ minerals formed on control silk membrane (no peptides).
FIG. 3b shows a crystal obtained after removal of silk.

"Aligned", as described herein, is the regular, controlled or uniform mineralization of the inorganic crystals on the surface of the template. For example, FIG. 2 illustrates an aligned coating while the crystal coating in FIG. 3 is not aligned.

Proteins useful for the protein template include structural proteins such as keratins, collagens and silks.

Preferably, the protein template comprises a silk fibroin. Depending on the use of the mineralized protein template, the silk fibroin can be processed into, for example, silk fibers (e.g., electrospun) silk threads, silk hydrogels, silk foams, silk meshes, or into three-dimensional porous silk matrices.

The anionic polymers interact with the protein template to establish a surface that promotes more regular nucleation and growth of inorganic crystals and include any anionic polymer capable of nucleating the mineral used to form the inorganic coating. In the absence of the anionic component only irregular inorganic surfaces are formed, while regular controlled surfaces form in the presence of this component. The anionic polymer can be mixed with the template during the processing or formation of the template, e.g. mixed in the silk fibroin solution prior to casting a film or forming a fiber, gel, or three-dimensional porous matrix. Alternatively, the anionic polymer can be adsorbed or incorporated into or onto a formed template by, for example, soaking the template in an anionic polymer solution. Preferred anionic polymer interfaces include polyaspartic acid, polyacrylic acid and alginic acid.

Preferably, the amount of anionic polymer to protein can range from 0.1 mg/g of protein up to 1:1 or higher.

According to methods of the invention, an inorganic coating is then formed on the template by contacting the template that has an anionic polymer interface with an inorganic material for a sufficient time period to allow mineralization of the inorganic coating. The steps for mineralization can be performed multiple times.

The inorganic material is preferably an inorganic salt that interacts with the anionic polymer. Most preferred inorganic materials include hydroxyapatite, silica, iron, cadmium, gold salts, and calcium carbonate.

In a further embodiment, the template is pre-organized to allow formation of aligned inorganic coated fibers or aligned 2D or 3D surfaces (for example, see FIGS. 10 and 11 showing aligned inorganic coatings on a stretched silk matrix and on aligned silk fibers respectively). The template can be pre-organized by stretching (e.g. stretching of films).

In one preferred embodiment, the template is removed after mineralization of the inorganic salt leaving hollow tubes or sheets.

As used herein, the term "fibroin" includes silkworm fibroin and insect or spider silk protein (Lucas et al., *Adv. Protein Chem* 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavipes*. In the alternative, the silk proteins suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

Methods for generating silk fibers, films, gels, foams, meshes, and three-dimensional porous matrices are well known in the art. See, e.g. Altman, et al., *Biomaterials* 24:401, 2003; PCT Publications, WO 2004/000915 and WO 2004/001103; and PCT Application No's PCT/US/04/11199 and PCT/USA04/00255, which are herein incorporated by reference.

Preferably, a concentrated silk fibroin solution free of organic solvent is used. See, e.g. PCT Application number PCT/US/04/11199.

Preferably, before contact with an aqueous solution, the silk fibroin template is treated to induce an amorphous β-sheet conformation transition. Such treatments include, for example, immersion in methanol or stretching. 100% methanol can be used.

Biocompatible polymers can be added to the silk solution to generate composite templates in the process of the present invention. Biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387, 413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). Two or more biocompatible polymers can be used.

In one preferred embodiment, additives such as pharmaceutical/therapeutic agents, or biologically active agents, are incorporated into the template or into the inorganic coating. For example, growth factors, pharmaceuticals, or biological components can be incorporated into the template during the formation of the silk film, fiber, foam, gel, thread, mesh, or three-dimensional matrix. Alternatively, additives can be added during the crystallization process of the inorganic coating, or can be coated onto the template with an aligned inorganic coating after its' formation. Additives can also be loaded into or onto the inorganic coating after removal of the template.

The variety of different pharmaceutical/therapeutic agents that can be used in conjunction with the methods of the present invention is vast and includes small molecules, proteins, antibodies, peptides and nucleic acids. In general, therapeutic agents which may be administered via the invention include, without limitation: anti-infectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); anti-angiogenic proteins such as endostatin, and other naturally derived or genetically engineered proteins, polysaccharides, glycoproteins, or lipoproteins. Growth factors are described in The Cellular and Molecular Basis of Bone Formation and Repair by Vicki Rosen and R. Scott Thies, published by R. G. Landes Company, hereby incorporated herein by reference. Additionally, the templates of the present invention can be used to deliver any type of molecular compound, such as, pharmacological materials, vitamins, sedatives, steroids, hypnotics, antibiotics, chemotherapeutic agents, prostaglandins, and radiopharmaceuticals. The present invention is suitable for delivery the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

The therapeutics/pharmaceuticals of the invention may be formulated by mixing with a pharmaceutically acceptable carrier. Any pharmaceutical carrier can be used that does not dissolve the template and/or inorganic coating. The therapeutic agents, may be present as a liquid, a finely divided solid, or any other appropriate physical form.

Examples of other biologically active agents suitable for use in the methods of the invention include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials November; 24(24):4385-415); biologically active ligands; and substances that enhance or exclude particular varieties of cellular or tissue ingrowth. Such additives are particularly useful, in tissue engineering applications. For example, the steps of cellular repopulation of a 3-dimensional scaffold matrix preferably are conducted in the presence of growth factors effective to promote proliferation of the cultured cells employed to repopulate the matrix. Agents that promote proliferation will be dependent on the cell type employed. For example, when fibroblast cells are employed, a growth factor for use herein may be fibroblast growth factor (FGF), most preferably basic fibroblast growth factor (bFGF) (Human Recombinant bFGF, UPSTATE Biotechnology, Inc.). Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-β and the like.

The resultant matrices can then be used to deliver therapeutic agents to cells and tissues. The ability to incorporate, for example pharmaceutical agents, growth factors and other biological regulators, enzymes or possibly even cells in the construct of the present invention provides for stabilization of these components for long term release and stability, as well as better control of activity and release.

In yet another aspect the present invention provides a method for forming an aligned inorganic coating on a template comprising contacting the template with poly-L-aspartic acid followed by calcium carbonate for a sufficient period of time to allow mineralization of the calcium carbonate thus forming an inorganic coating on the template.

Finally, there is also provided a product produced by the methods described herein.

The products produced by these methods offer new options in the formation of scaffolds for biomaterials and tissue engineering applications. While the templates are useful in and of themselves, the ability to form inorganic coatings with controlled thickness leads to control of mechanical properties (e.g., stiffness) and biological interactions, such as for bone formation. Furthermore, the ability to control these processes allows one to match structural and functional performance of scaffolds for specific tissue targets and needs.

As noted above, the underlying template (e.g., protein) can be removed or etched away to generate porous networks, tubes, or lamellar sheets of inorganic material. These materials are useful directly as biomaterial scaffolds, for control of cell and tissue growth (e.g., as nerve conduits, bone conduits) and for nonbiological applications (e.g., filtration and separation media, catalysis, decontamination (directly of if filled with appropriate chemical or enzymes), radar chaff, coatings in general, and many related needs—for example, inorganic fillers to toughen materials that can also be filled with a second component.

By combining different matrix materials and mediating peptides, the method of the present invention can be used in the preparation of aligned silica, hydroxyapatite, and calcium carbonate nanotubes. The process can also be used in the nucleation and growth of inorganic materials, i.e. iron, cadmium, and gold salts, among others, with appropriately selected peptides (e.g., histidine-rich, ferratin-like, cysteine-containing).

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

Methods for Forming Silk Protein Templates

The templates of the invention, for example the silk fibers, films, foams, gels, and three-dimensional matrices can be formed from concentrated silk fibroin solutions that are prepared in the absence of organic solvent. For example, a silk fibroin solution can be prepared by any conventional method known to one skilled in the art and dialyzed against a hygroscopic polymer (e.g. polyethylene glycol (PEG), polyethylene oxide, amylase or sericin) for a sufficient time to result in an aqueous silk fibroin solution between 10-30% or greater. The concentrated silk fibroin solution can then be processed into the desired template as described in more detail below. Alternatively, means known in the art using organic solvents can be used.

Silk film templates can be produced by casting an aqueous silk fibroin solution. In one embodiment, the film is contacted with water or water vapor, in the absence of alcohol. The film can then be drawn or stretched mono-axially or biaxially. The stretching of a silk blend film induces molecular alignment of the film and thereby improves the mechanical properties of the film. Preferably, the resulting silk blend film is from about 60 to about 240 μm thick, however, thicker samples can easily be formed by using larger volumes or by depositing multiple layers.

Foams may be made from methods known in the art, including, for example, freeze-drying and gas foaming in which water is the solvent or nitrogen or other gas is the blowing agent, respectively. Alternately the foam is made by contacting the silk fibroin solution with granular salt. The pore size of foams can be controlled, for example by adjusting the concentration of silk fibroin and the particle size of a granular salt (for example, the preferred diameter of the salt particle is between about 50 microns and about 1000 microns). The salts can be monovalent or divalent. Preferred salts are monovalent, such as NaCl and KCl. Divalent salts, such as $CaCl_2$ can also be used. Contacting the concentrated silk fibroin solution with salt is sufficient to induce a conformational change of the amorphous silk to a β-sheet structure that is insoluble in the solution. After formation of the foam, the excess salt is then extracted, for example, by immersing in water. The resultant porous foam can then be dried and the foam can be used, for example, as a cell scaffold in biomedical application.

In one embodiment, the foam is a micropatterned foam. Micropatterned foams can be prepared using, for example, the method set forth in U.S. Pat. No. 6,423,252, the disclosure of which is incorporated herein by reference. The method comprises contacting the concentrated silk solution with a surface of a mold, the mold comprising on at least one surface thereof a three-dimensional negative configuration of a predetermined micropattern to be disposed on and integral with at least one surface of the foam, lyophilizing the solution while in contact with the micropatterned surface of the mold, thereby providing a lyophilized, micropatterned foam, and removing the lyophilized, micropatterned foam from the mold. Foams prepared according this method comprise a predetermined and designed micropattern on at least one surface, which pattern is effective to facilitate tissue repair, ingrowth or regeneration.

Fiber templates may be produced using, for example, wet spinning or electrospinning. Alternatively, as the concentrated solution has a gel-like consistency, a fiber can be pulled directly from the solution.

Electrospinning can be performed by any means known in the art (see, for example, U.S. Pat. No. 6,110,590). Preferably, a steel capillary tube with a 1.0 mm internal diameter tip is mounted on an adjustable, electrically insulated stand. Preferably, the capillary tube is maintained at a high electric potential and mounted in the parallel plate geometry. The capillary tube is preferably connected to a syringe filled with silk solution. Preferably, a constant volume flow rate is maintained using a syringe pump, set to keep the solution at the tip of the tube without dripping. The electric potential, solution flow rate, and the distance between the capillary tip and the collection screen are adjusted so that a stable jet is obtained. Dry or wet fibers are collected by varying the distance between the capillary tip and the collection screen.

A collection screen suitable for collecting silk fibers can be a wire mesh, a polymeric mesh, or a water bath. Alternatively and preferably, the collection screen is an aluminum foil. The aluminum foil can be coated with Teflon fluid to make peeling off the silk fibers easier. One skilled in the art will be able to readily select other means of collecting the fiber solution as it travels through the electric field. The electric potential difference between the capillary tip and the aluminum foil counter electrode is, preferably, gradually increased to about 12 kV, however, one skilled in the art should be able to adjust the electric potential to achieve suitable jet stream.

The fiber may also be formed into yarns and fabrics including for example, woven or weaved fabrics. Alternatively, the fibers may be in a non-woven network.

Silk hydrogel templates can be prepared by methods known in the art. The sol-gel transition of the concentrated silk fibroin solution can be modified by changes in silk fibroin concentration, temperature, salt concentrations (e.g. $CaCl_2$, NaCl, and KCl), pH, hydrophilic polymers, and the like. Before the sol-gel transition, the concentrated aqueous silk solution can be placed in a mold or form. The resulting hydrogel can then be cut into any shape, using, for example a laser.

3-dimensional porous silk matrix templates may be made by (a) gas foaming, and (b) solvent casting/particulate leaching (Freyman et al. *Progress in Materials Science* 2001; 46:273-282; Mikos et al. *Electronic Journal of Biotechnology*, Accurate, 2000; 3:No. 2; Thomson et al. Biomaterials, 1998; 19:1935-1943; Widmer et al. *Biomaterials,* 1998; 19:1945-1955; Zhang R.& Ma P. *Journal of Biomedical Material Science,* 1999; 44:446-455; Nam et al. *Journal of Applied Polymer Science*, Vol. 81, 3008-30021, (2001); Agrawal et al. *Journal of Biomedical Material resources* 2001, 55, 141-150; Harris et al. *Journal of Biomedical Material Research* 1998, 42, 396-402; Hutmacher D. *Journal of biomaterial science polymer science* Edn 2001. 12, 107-124).

One preferred method for material fabrication is leaching. The solvent casting/particulate leaching method involves mixing a water-soluble porogen, for example, NaCl with a viscous silk polymer solution (Freyman et al. Progress in Materials Science 2001; 46:273-282; mikos et al. *Electronic Journal of Biotechnology*, Accurate, 2000; 3:No. 2; Agrawal et al. *Journal of Biomedical Material resources* 2001, 55, 141-150; Hutmacher D. *Biomaterials* 2000. 21, 2529-2543; Hutmacher D. *Journal of biomaterial science polymer science* Edn 2001. 12, 107-124). The mixture is cast into a Teflon container where the solvent is evaporated. The result is a salt/polymer composite. The composite is immersed in water to leach out the salt, resulting in a porous three-dimensional structure.

EXAMPLES

Example I

Mineralization of $CaCO_3$ on Poly(asparticacid) Soaked Silk Fiber

Materials and Methods

Cocoons of *B. mori* silkworm silk were kindly supplied by M. Tsukada, Institute of Sericulture, Tsukuba, Japan. PEO with an average molecular weight of $9 \times 10^5$ g/mol (Aldrich) was used in blending. $CaCl_2$, ammonium carbonate, and poly-L-aspartic
acid (sodium salt, MW 11,000) and poly-L-glutamic acid (sodium salt, MW 10900) were obtained from Sigma.
Preparation of Electrospun Fiber Matrix
1. Fiber Matrix without Poly-Asp Silk membranes composed of nanoscale fibers (less than 600 nm in diameter) were fabricated from aqueous silk solutions with PEO by electrospinning as described earlier[6]. The obtained membrane was immersed into a 90/10(v/v) methanol/water solution for 10 min to induce an amorphous to β-sheet conformational transition of electrospun silk fiber and then washed with water for 24 hours at 37° C. to remove PEO. This process was performed in a shaking incubator and shaking speed was 50 rpm. It was expected that just PEO phase would dissolve from the each fiber. The obtained membrane was used for mineralization.
2. Fiber Matrix with Poly-Asp Poly-Asp was added into silk/PEO solution before electrospinning. The obtained membrane was used for mineralization directly without PEO extraction.
Mineralization on Fiber Matrix Pieces of silk matts ($\approx 0.5$ cm$^2$) were placed in 12-well Tissue culture dishes (untreated, well surface area of 3.8 cm$^2$). A calcium chloride solution (10 mM, 1.5 mL) containing different amounts of poly-Asp(<10 mg) was introduced into the wells and incubated for 24 hours at room temperature on a rocking table. Following the removal of the peptide solution, the silk matt was introduced into a fresh well and overlaid with $CaCl_2$ (10 mM) solution. The wells were covered with Parafilm, which was punctured with a needle.

Crystallization was induced by slow diffusion of ammonium carbonate vapor into 10 mM $CaCl_2$ in a closed desiccator. $(NH_4)_2CO_3$ powder was placed in four wells of a 12 well tissue culture dish. Slow diffusion was achieved through needle holes in the Parafilm covering the culture dishes. The experiments were run at 18±1° C.

For experiments using peptide-incorporated membrane, the matt containing poly-Asp was used directly for mineralization. For control experiment, silk matt without peptide treatment was used.
Scanning Electron Microscope (SEM)

Silk fibers and minerals formed were examined using LEO Gemini 982 Field Emission Gun SEM for morphology analysis. The surfaces of the specimens were coated with gold before SEM observation for some samples. Deproteinated samples were obtained by treatment with sodium hypochlorite.
X-ray Diffraction (XRD)

WAXD experiments employing CuKa radiation on silk fibers and minerals formed were done using Bruker D8 Discover X-ray diffractometer with GADDS multiwire area detector. 40 kV and 20 mA and 0.5 mm collimator was used.
Transmission Electron Microscope (TEM)

Figure 1:
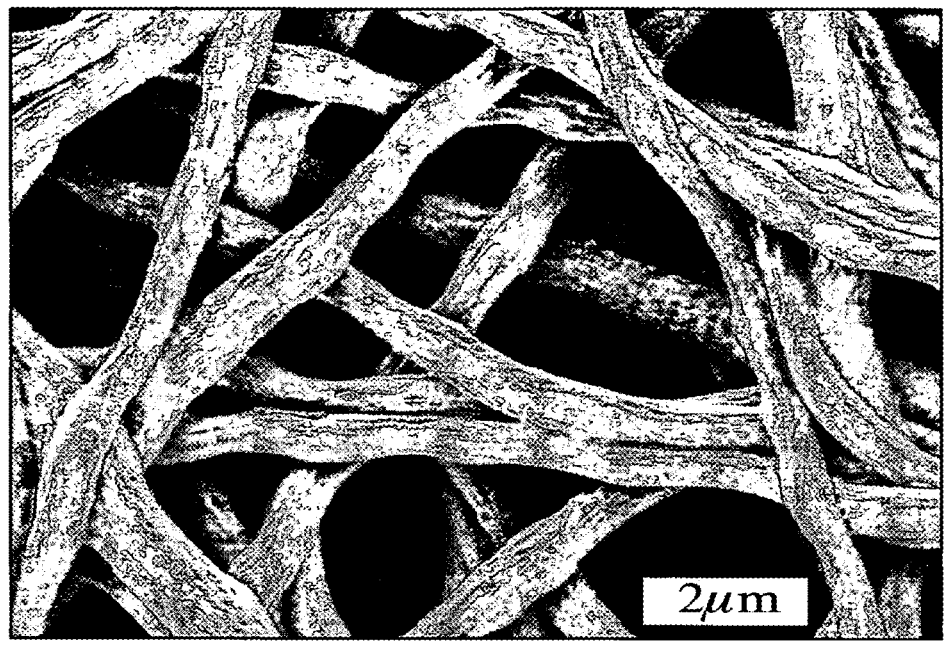
FIG. 1 shows a scanning electron micrograph of electrospun fiber after methanol treatment (no peptides).

Silk fibers after mineralization were stained with osmium tetroxide vapor until it turned dark yellow. The stained silk fibers were then embedded in Epon resin and left at 60° C. for 24 hours. Thin TEM sample slices were made by microtoming and observed with Philips CM-10 TEM.
Results and Discussion
1. Silk Membrane Characterization The silk matrix with nanoscale fibers was produced through electrospinning process. The fibers have a size of 500±100 nm (FIG. 1), which is about 40 times smaller than that of the native silk fibers after extraction of sericin.

After methanol treatment, the silk fiber matrix became water insoluble and collapsed resulting in a densely packed mat. However, it was observed that the fiber mat swells in aqueous solution, which makes it useful as matrix for mineral growth. The aqueous solution containing the mineralization species filled the interfiber space, creating local environment for mineralization. In addition, the swollen hydrated fiber mat contracted approxiamately to its original dimension when dried in air.
2. Silk-$CaCO_3$ Composite Silk is a highly hydrophobic biopolymer, which is incompatible with the charged and hydrated nature of the calcium carbonate surface. In this study, the silk surface is functionalized with poly-Asp to generate a suitable surface to induce calcium carbonate nucleation. In one case, the silk fiber was soaked in a poly-Asp solution resulting the adsorption of the peptides. In the other case, the poly-Asp acid was blended in the silk solution before electrospinning process. In both cases, the silk composite consisting of a silk fiber core and a mineral coating was obtained.
Case 1: Mineralization of $CaCO_3$ on Poly(aspartic acid) Soaked Silk Fiber After being soaked in poly-Asp for 24 hours at room temperature, the silk membrane was used for $CaCO_3$ mineralization. After 2 days of crystallization at 18±1° C., the fibers were coated with a uniform layer of $CaCO_3$ crystals at some areas of the membrane (FIG. 2). As contrast, crystals formed on the membrane without poly-Asp soaking were big crystals protruding from the membrane (FIG. 3). The deproteinated sample showed that the big crystals are composed of two parts. One part of the crystals were embedded in the silk membrane with tubular cavity in the shape of fiber, and the other part is in the form of regular rhombohedral calcite crystal morphology. It is apparent that the crystal nuclei formed inside the membrane cavity locally and the continuous growth inside the membrane led to the tubular structure.

With peptide adsorption, the fiber surface became negatively charged because of the carboxylate groups on the side chain of poly-Asp. It is reported that the poly-Asp adopted a β-sheet structure under our experimental conditions[7, 12-16]. Falini et al. use gelatin films with entrapped poly-Asp to induce the crystallization of different polymorphs of calcium carbonate[12-16] and the oriented crystallization is controlled by the β-sheet structure assumed by poly-Asp. Poly-Asp favors a α-Helical structure[17, 18] and undergoes a conformational change to β-sheet once binding $Ca^{2+}$. This conformation change might facilitate the anchor of the peptides onto silk surface that also adopts β-sheet conformation. The arrangement of the peptides might provide a form of interfacial complementarity in which the charge distribution between anions and cations in planes of the mineral lattice is mimicked by the surface arrangement ions bound to peptides exposed at the fiber surface. The activation energy of nucleation was then lowered and led to nucleation on the fiber surface. If the silk matrix was soaked in poly-Asp solution for short period (30 min), big crystals formed instead of small crystals growing from the fiber surface. Another factor affecting the nucleation of $CaCO_3$ on fiber surface could be the surface roughness of the fiber, which is observed on the fiber surface after PEO extraction. The concave features on fiber surface can give rise to a high spatial charge density and three-dimensional clustering of $Ca^{2+}$ and are good nucleation sites.

The free poly-Asp trapped inside the silk matrix macromolecules coordinates with the adsorbed peptides to mediate the mineralization. If the silk fiber matrix was washed with $CaCl_2$ solution after soaking in poly-Asp solution (in $CaCl_2$) or the moisture trapped inside the matrix was removed by filter paper, big $CaCO_3$ crystals appeared (data not shown). In contrast, if the peptide-soaked silk fiber matrix was used directly, the silk fiber was coated with $CaCO_3$ minerals. To further verify the importance of the existence of the free poly-Asp, experiments by soaking the silk mat in $CaCl_2$ solution with different amounts of peptides were carried out. Coating of the fiber is only obtained at a high level of poly-Asp. The anchored peptides act as template for the growth of minerals while free poly-Asp can inhibit the growth of the minerals towards the bulk solution, which leads to the coating of minerals on silk fiber. This template-inhibition mechanism also applied to the situation of formation of inorganic film on two-dimensional substrates.

Figure 4:
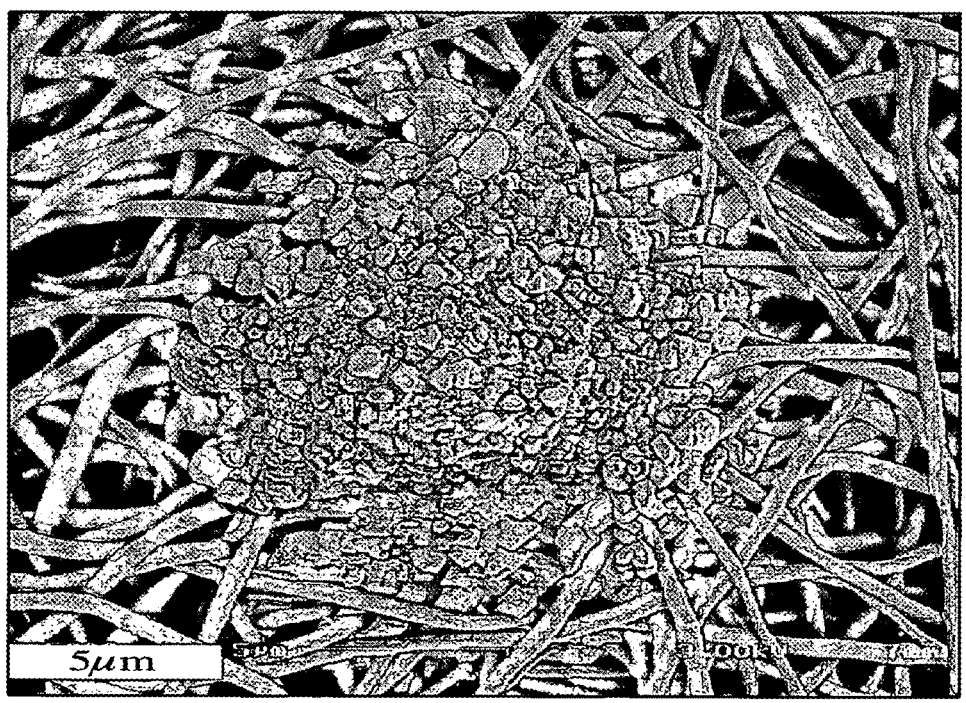
FIG. 4 shows $CaCO_3$ minerals formed on poly (glutamic acid) soaking silk fiber.

The importance of polypeptide conformation on the crystallization of calcium carbonate was evaluated by comparing the behavior of poly-Asp with those of poly (glutamatic acid) (poly-Glu) and monomer of poly-Asp, aspartic acid. Poly-Glu adopts random coil conformation in the conditions where the poly (aspartic acid) adopts β-sheet conformation. FIG. 4 showed how the adsorption of the poly-Glu influences the crystallization of $CaCO_3$. No uniform coating of $CaCO_3$ was obtained. In the case of simple aspartic acid, no big difference was observed compared with the control experiment without peptides (FIG. 5), which may be due to the poor adsorption on silk surface and retention inside silk matrix.

Figure 7:
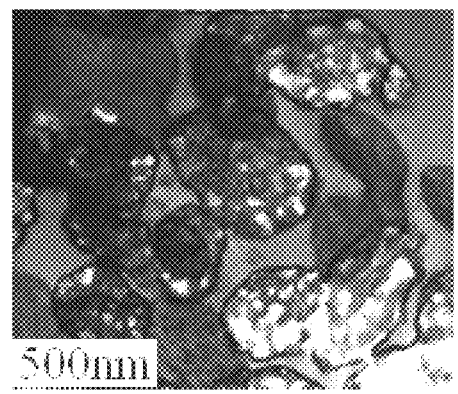
FIG. 7 shows TEM images of silk fiber after mineralization.
Figure 8A:
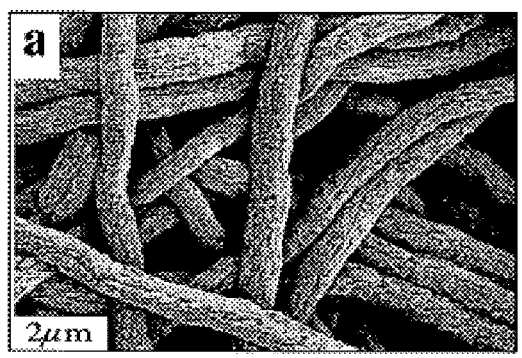
FIGS. 8 a-d show minerals formed on a poly-Asp incorporated silk fiber with 10 mg poly-Asp/g silk: (a) before, (b) after removal of silk and 200 mg poly-Asp/g silk: (c) before, (d) after removal of silk.
Figure 8B:
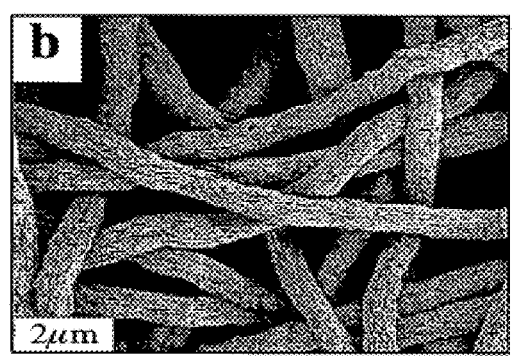
Figure 8C:
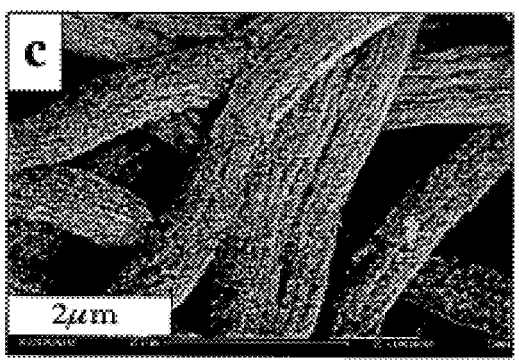
Figure 8D:
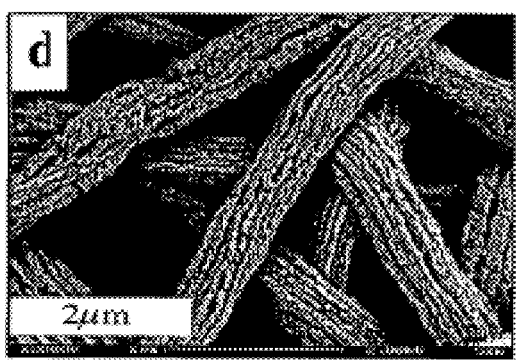

An interesting feature that can be observed from SEM analysis is the expansion of the fiber during mineralization. Pores were observed on partially coated fiber (FIG. 6 *a*) or at the end of the coated fiber (FIG. 6*b*). TEM (FIG. 7) images also showed big pores on the cross section of the coated fiber, while pore size is smaller in the case of uncoated fiber. The electrospun fiber has porous structure. The continuous crystal growth in the tangential and radial direction around the fiber convex surface caused the fiber expansion leaving bigger pores inside fiber. After the $CaCO_3$ minerals were dissolved by treatment with 1M HCl, SEM analysis showed that the fiber resumed its original size. This indicated the strong interaction between the crystals and the fiber surface and the crystals formed on fiber surface via epitaxial growth.

Figure 9A:
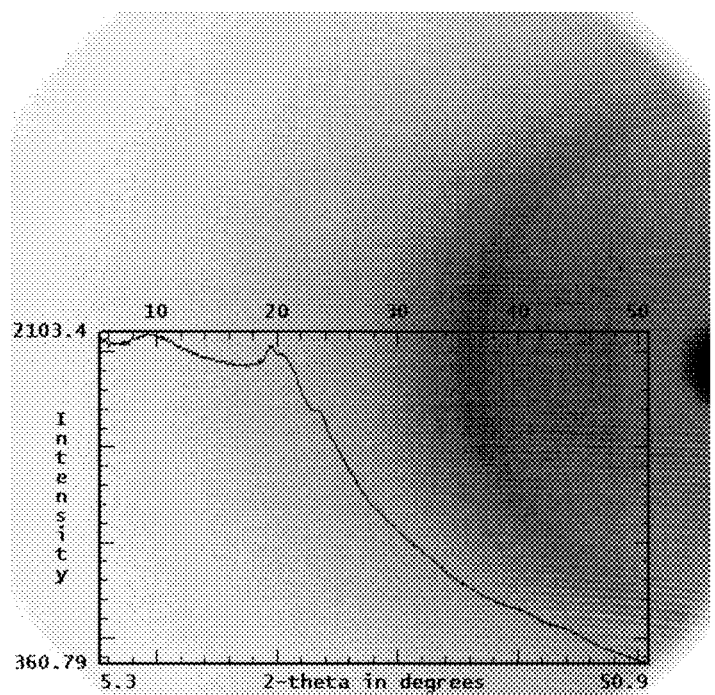
FIGS. 9 a and 9b show X-ray diffraction pattern of silk matrix before (a) and after mineralization (b).
Figure 9B:
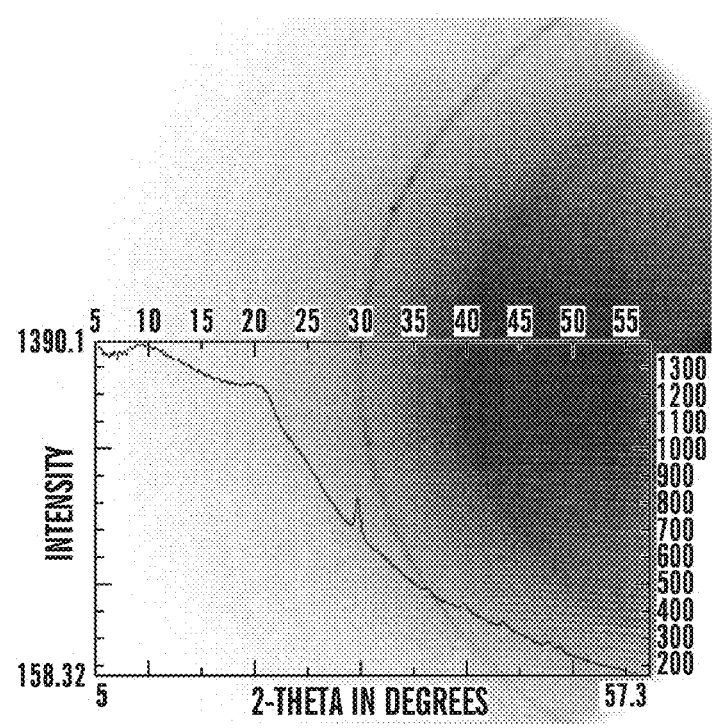
Figure 12A:
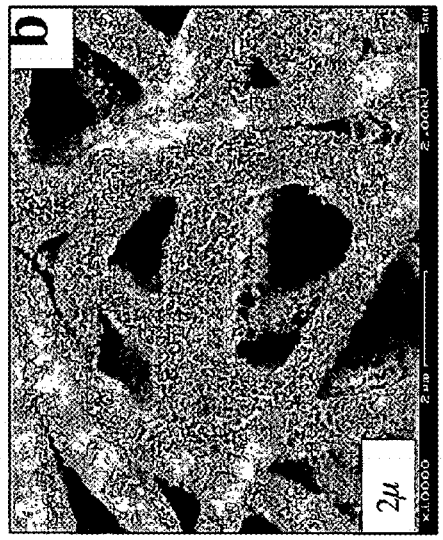
FIGS. 12 a-d show SEM images of apatite coating on silk fibers with different concentrations of poly-L-aspartic acid: (a) 0, (b) 10, (c) and (d) 200 mg/g silk after one cycle of 10 minute soaking.
Figure 12B:
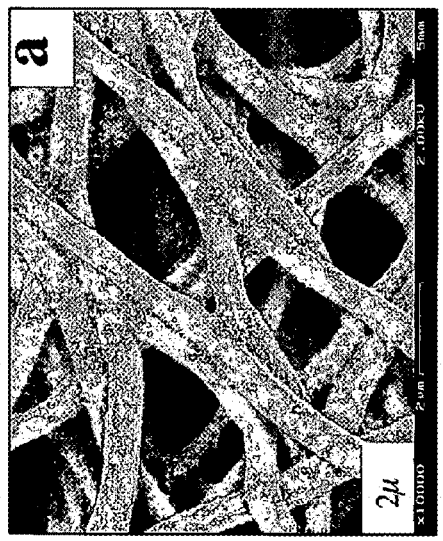
Figure 12C:
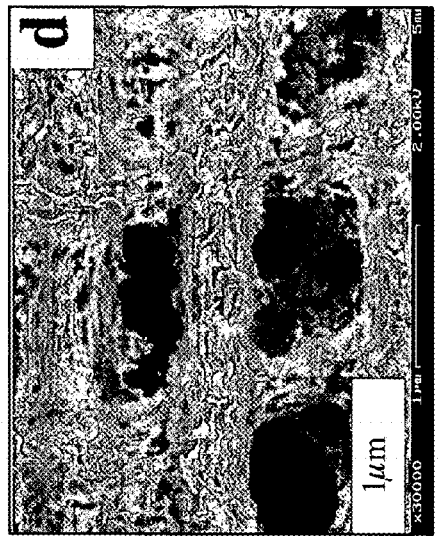
Figure 12D:
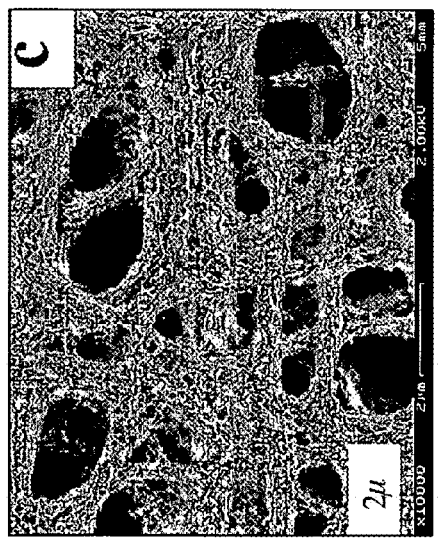
Figure 13B:
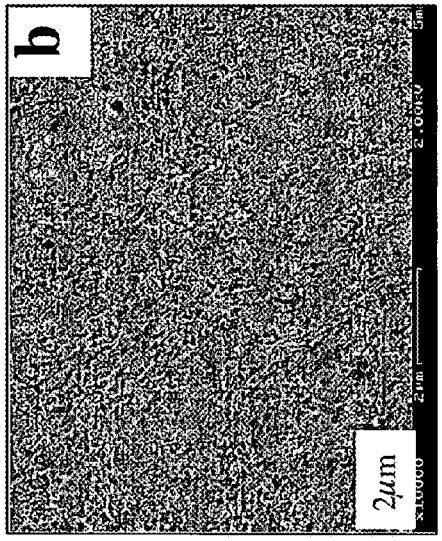
FIGS. 13 a-d show SEM images of apatite coating on silk fibers with 200 mg poly-Asp/g silk after different soaking periods and cycles: (a) 1 minute, 1 cycle, (b) 10 minutes, 3 cycles, (c) 1 hour, 1 cycle, and (d) 1 hour, 3 cycles.
Figure 13D:
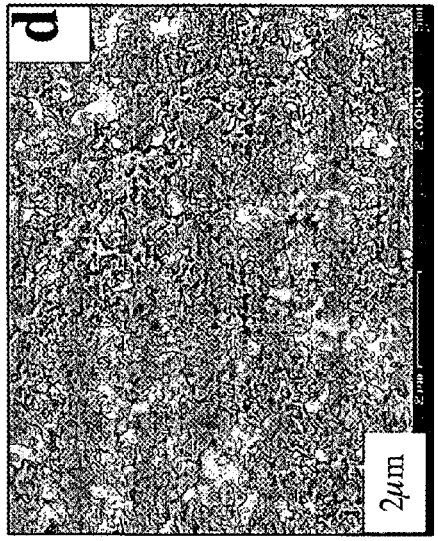
Figure 13A:
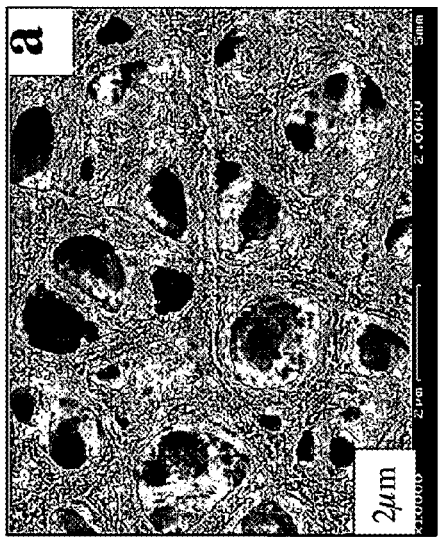
Figure 13C:
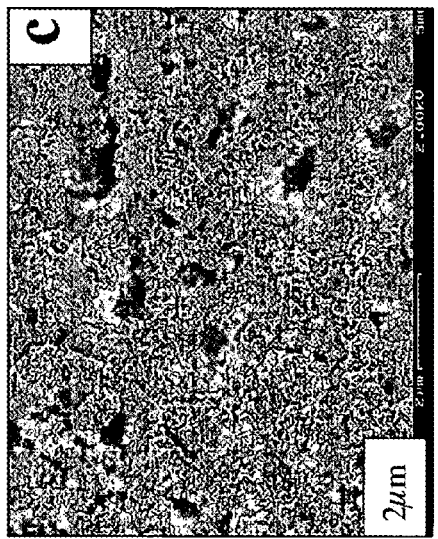
Figure 14A:
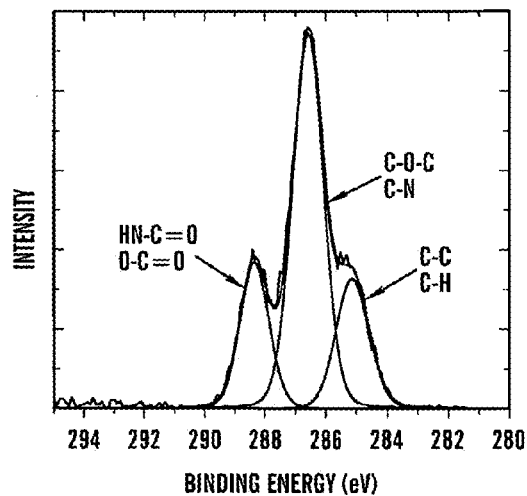
FIGS. 14 a-d show an X-ray photoelectron narrow-scan of the C1s and O1s region of silk electrospun fiber mats. 14a, C1s 200 mg poly-L-asp/g silk; 14b, C1s 0 mg/poly-L-asp/g silk; 14c, O1s 200 mg poly-L-asp/g silk; 14d, O1s 0 mg/poly-L-asp/g silk.
Figure 14C:
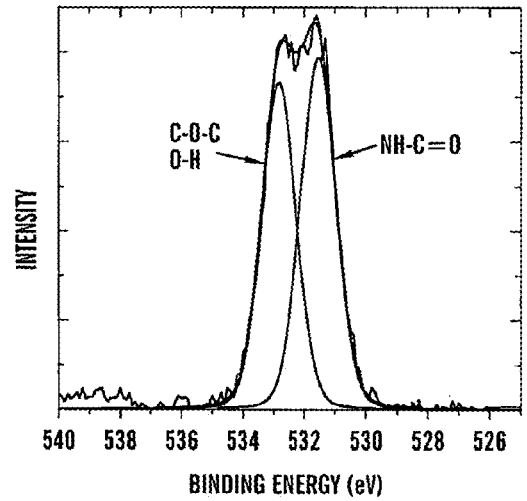
Figure 14B:
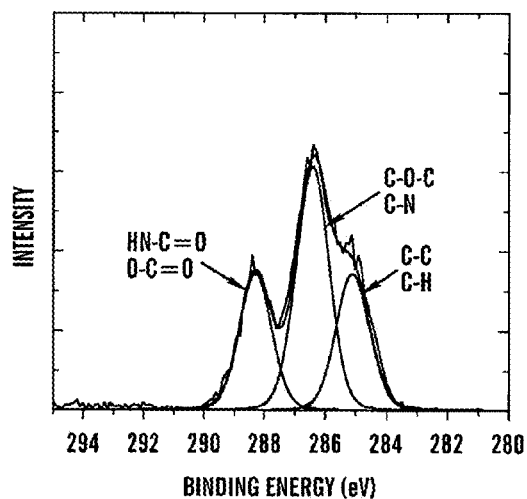
Figure 14D:
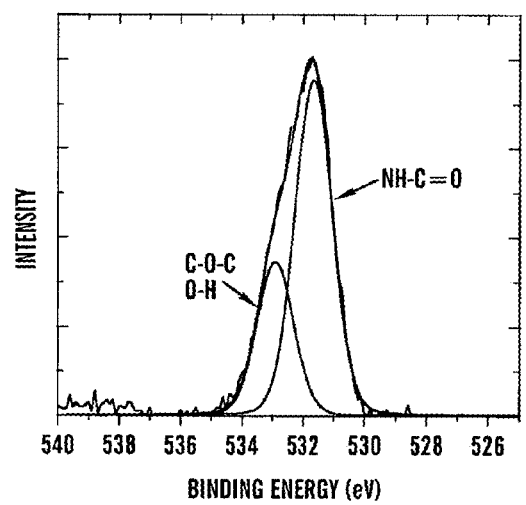
Figure 15A:
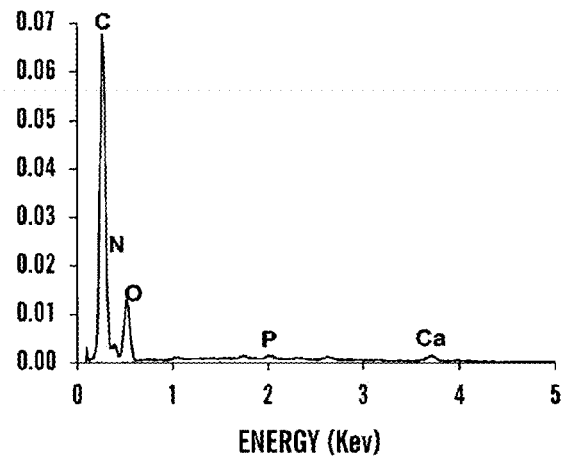
FIGS. 15 a-d show EDS spectra of minerals deposited on fiber mats (200 mg poly-L-aspartic acid/g silk) with (a) 10 min, 1 cycle (b) 10 min, 3 cycles, (c) 1 hr, 1 cycle, (15d) 1 hr, 3 cycles.
Figure 15C:
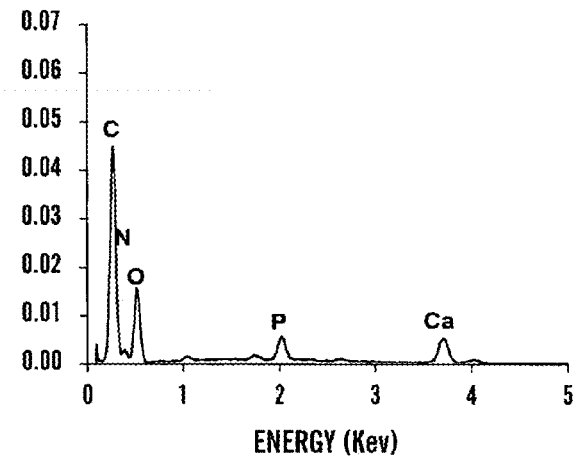
Figure 15B:
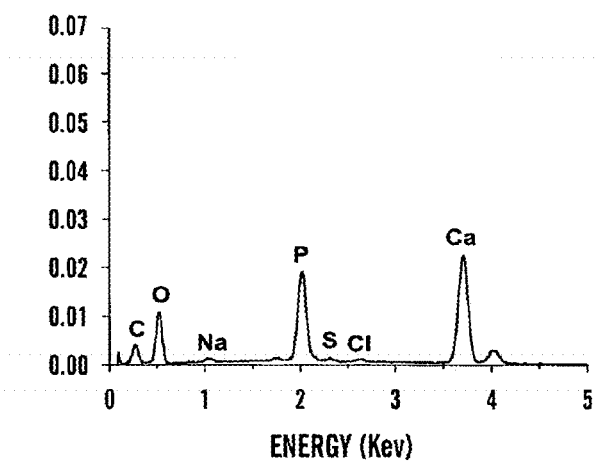
Figure 15D:
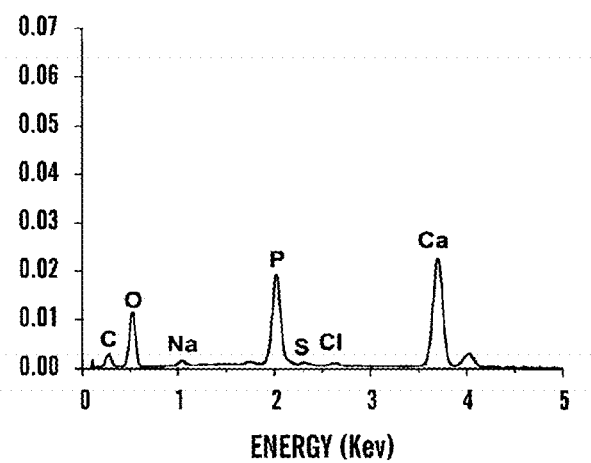
Figure 16A:
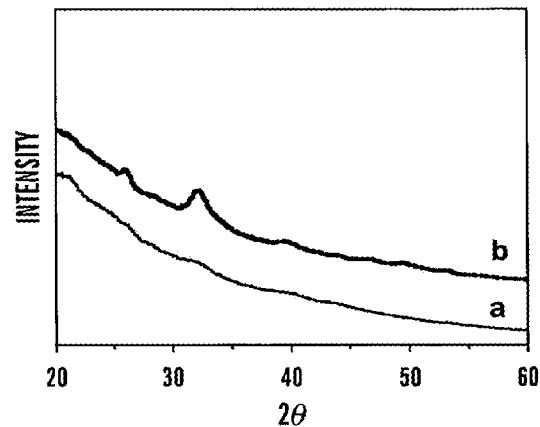
FIGS. 16 a-d shows X-ray diffraction patterns of silk fibers after apatite deposition: 16a shows line (a) no poly-L-asp, 10 minutes, 1 cycle and line (b) no poly-L-asp, 10 minutes, 3 cycles; 16b shows line (c) 200 mg poly-L-asp/g silk, 10 minutes, 1 cycle and line (d) 200 mg poly-L-asp/g silk, 10 min, 3 cycles; 16c shows line (e) 200 mg poly-L-asp/g silk, 1 hour, 1 cycle and line (f) 200 mg poly-L-asp/g silk, 1 hour, 3 cycles; 16d shows line (g) hydroxyapatite standard.
Figure 16B:
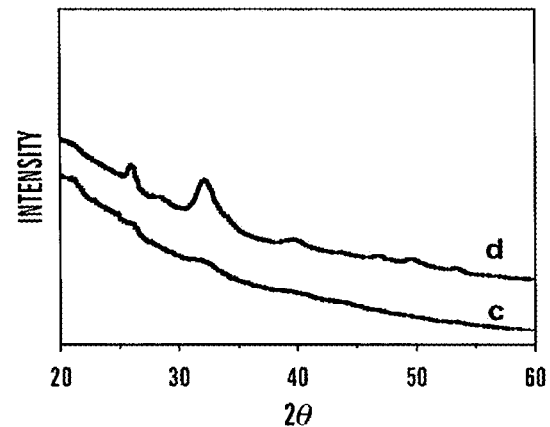
Figure 16C:
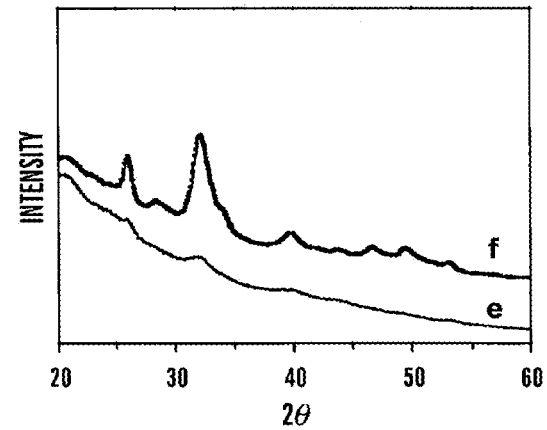
Figure 16D:
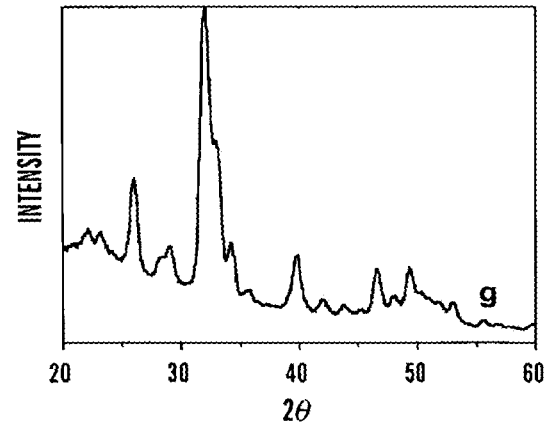

Case 2: Mineralization of $CaCO_3$ on Poly (Aspartic Acid) Incorporated Silk Fiber A layer of $CaCO_3$ crystals was also formed on the poly-Asp incorporated fibers (FIG. 8). Compared to case 1, this is a more efficient method to improve the attachment of peptides on silk fiber surface. Normally, a large amount of peptides is needed to reach a high adsorption of the poly-Asp. The growth of the crystals on peptide incorporated fibers aligned along the fiber axis, which may be due to the orientation of the poly-Asp and silk molecules. The fiber showed some birefringence under polarized microscope before methanol treatment. It is generally assumed that in silk, birefringence is positively correlated with molecular orientation and density, forming more so called 'β-sheet crystal areas'[19]. In the case of electrospun fiber, the birefringence is caused by the orientation of silk molecule, but not necessarily forming β-sheet structure, because FTIR does not show adsorbsion peaks for β-sheet structure. It is possible that poly-Asp also adopted orientation along fiber axes during the electrospinning. The phase separation of silk and PEO leads to parallel silk and PEO bands on fiber surface. The aligned poly-Asp forms a gel-like structure along the silk fiber and triggers the nucleation of minerals, while released poly-Asp suppress the growth. Therefore, the aligned growth of minerals was obtained. The mineralized silk fibers were characterized by X-ray diffraction (XRD) and the inorganic phase observed was calcite (FIG. 9). Since fibers are orientated randomly and the curved feature of the fiber, no specific orientation of inorganic crystals was observed by XRD.

Case 3: Mineralization of $CaCO_3$ on Stretched (Orientated) Silk Fiber

By stretching the silk fibrous mat, it is possible to orientate the fibers (FIG. 10). In this way, an aligned silk matrix is obtained and used as matrix ordered material structure synthesis. Unlike the non-stretched fiber, the stretched fiber become partially water-insoluble after stretching even without methanol treatment, which suggest that the stretching can improve the molecular orientation of fiber. After mineralization, an ordered fibrous silk-$CaCO_3$ composite structure was obtained (FIG. 11). By removing the silk component, an ordered inorganic structure of $CaCO_3$ fiber can be obtained.

Case 4: Apatite Growth on Electrospinning Silk Fibers

An alternative soaking process was used to deposit apatite on silk fibers[20, 21]. First, a silk mat of 5×10 mm was soaked in 200 mM $CaCl_2$ solution (buffered with 50 mM Tris·HCl, pH 7.4 at 37° C.) for predetermined period of time. The silk mat was then transferred to a 120 mM $Na_2HPO_4$ solution after excessive moisture was removed by blotting on filter paper and soaked the predetermined period of time. Soaking was repeated for a specific number of cycles.

Aligned growth of the apatite along fiber axes was obtained when the poly-L-aspartic acid concentration was 200 mg/g silk (FIG. 12). As comparison, scattered apatite particles were deposited on silk fibers without poly-L-aspartic acid and only randomly oriented apatite particles formed on silk fibers at a low concentration of poly-L-aspartic acid. FIG. 13 showed the effect of soaking period and cycles on the deposition of apatite on silk fibers. EDS (X-ray Energy-Dispersive Spectroscopy) and XRD analysis of samples after 10 minutes/3 cycles soaking showed the minerals formed were hydroxyapatite. A Ca/P ratio of 1.67 was obtained by EDS, which is characteristic of hydroxyapatite. XRD pattern also revealed that hydroxyapatite formed on silk fibers.

Example II

Silk Apatite Composites from Electrospun Fibers

The objective of the present example was to use electrospun silk fibers as nucleation template for growth of apatite as a route to generate new biomaterials with potential utility for bone-related applications. The electrospinning process offers an alternative approach to protein fiber formation that can generate nanometer diameter fibers, a useful feature in some biomaterial and tissue engineering applications due to the increased surface area[42-46]. Electrospinning has been utilized to generate nanometer diameter fibers from recombinant elastin proteins[47], silk-like proteins[48-50], silkworm silk fibroin[51], type I collagen[45,52,53] and spider dragline silk[54]. If electropsun polymer fibers generate structures suitable for control of functional group patterning, then such templates should be effective for apatite nucleation and crystal growth, leading to new protein-based composites. Since silk fibroin self organizes due to hydrophilic/hydrophobic triblock sequences[55], pattern control is a controllable outcome[56]. In the present example, the controlled growth of apatite on electrospun silk fibroin fibers functionalized with poly-L-aspartic acid was demonstrated. Poly-L-aspartic acid was blended in the polymer aqueous solution prior to electrospinning. The structural and morphological details of these new composites are described, along with assessments of the mechanical properties of these new biomaterial composite matrices.

Materials and Methods

Cocoons of *B. mori* silkworm silk were kindly supplied by M. Tsukada, Institute of Sericulture, Tsukuba, Japan. PEO with an average molecular weight of $9 \times 10^5$ g/mol (Aldrich) was used in blending. $CaCl_2$, ammonium carbonate, poly-L-aspartic acid (sodium salt, Mw 11,000), and poly-L-lysine (Mw 22,000) were obtained from Sigma (St. Louis, Mo.). Hydroxyapatite standard was obtained from NIST (National Institute of Standards and Technology, Gaithersburg, Md.) with a Ca/P of 1.664±0.005.

Preparation of Electrospun Fiber Matrices

Silk membranes composed of nanoscale fibers were fabricated from aqueous silk solutions with PEO by electrospinning as described earlier[51]. The distance between the capillary tip and the collector was 21.5 cm and the applied voltage was 12 kV to generate electric field strength of 0.6 kV/cm. The flow rate of the blending solution was 0.02 ml/min. Poly-aspartic acid was added to silk/PEO solution before electrospinning. The electrospun mats obtained were immersed in 100% methanol for 5 mM to induce an amorphous to β-sheet conformational transition, required to preserve the intact membranes in aqueous solution during the subsequent mineralization steps.

Mineralization

The alternate mineralization process was used to nucleate and grow apatite on silk fibers[57]. First, a silk mat (5 mm×1 mm×50 μm) was soaked in 200 mM $CaCl_2$ solution (buffered with 50 mM Tris·HCl, pH 7.4 at 37° C.) for a predetermined period of time. The silk mat was then transferred to a 120 mM $Na_2HPO_4$ solution after excessive moisture was removed by blotting on filter paper and soaked for a predetermined period of time. This cycle was repeated depending on the specifics of the experiment.

I. Mechanical Properties

The mechanical properties of specimens were measured with an Instron 8511 servo-hydraulic-driven tension/compression/cyclic testing machine. All samples were stored in vacuum at room temperature before test. Each test was performed 5 times.

II. Characterization

Scanning of some specimens were coated with gold before SEM.

Electron Microscopy (SEM)

Silk fibers and minerals formed were examined using a LEO Gemini 982 Field Emission Gun SEM (Thornwood, N.Y.) for morphology analysis.

X-ray Diffraction (XRD)

Silk fibers and minerals were analyzed with a Bruker D8 Discover X-ray diffractometer (Billerica, Mass.) with GADDS multiwire area detector. WAXD (wide angle X-ray diffraction) experiments were performed employing CuKα radiation (40 kV and 20 mA) and 0.5 mm collimator. The distance between the detector and the sample was 47 mm.

X-ray Photoelectron Spectroscopy (XPS)

XPS was performed using a PHI 5600 ESCA microscope (Physical Electronics (PHI), Eden Prairie, Minn.). Spectra were typically acquired at a pressure below $2 \times 10^{-9}$ Torr using a monochromatized Al Kα source operating at 100 W. Pass energies used for survey and narrow scans were 187. 85 and 23.5 eV, respectively. Sample charging was compensated using fluxes of low energy electrons and positive argon ions.

X-ray Energy-Dispersive Spectroscopy (EDS)

The energy dispersive x-ray spectra were acquired using an EDAX Genesis system (Mahwah, N.J.) with a sapphire detector and a super ultra thin window. The SEM was a FEI Quanta 200 (Peabody, Mass.) tungsten filament system equipped with a EDAX Genesis energy dispersive x-ray spectrometer. The Quanta system was operated in conventional SEM mode. The x-ray spectra were collected for 100 seconds with an accelerating voltage of 20 kV, a time constant of 50 microseconds, and a resolution of 134 eV. The standardless quantification routine was used to determine the percent of elements present in the spectra.

Results and Discussion

Electrospun Silk/PEO Fibers

Electrospinning is an efficient fabrication process to assemble polymer mats composed of fibers with diameters ranging from several microns to less than 100 nm. In this electrostatic process, the polymer solution is subjected to a high-voltage electric field and small fibers are produced upon overcoming surface tension. The morphology and diameter of the electrospun silk/PEO fibers were examined using SEM. Fine, uniform fibers with diameters of 600±80 nm were obtained. The fiber orientation inside the nonwoven mat was random. The addition of the ionic poly-L-aspartic acid resulted in smaller fiber diameters (350±30 nm) because of the higher elongation forces caused by the higher charge density carried by the electrospinning jet.

XPS was used to determine the surface features of the electrospun fiber mat (Table 1).

TABLE 1

XPS Results from the electrospun silk fibers surfaces

| | O1s | | C1s | | N1s | | |
|---|---|---|---|---|---|---|---|
| Element | Bindign energy (eV) | Atom % | Bindign energy (eV) | Atom % | Bindign energy (eV) | Atom % | N1s/C1s |
| 1 | 530.9 | 21.7 | 284.6 | 61.1 | 398.4 | 15.3 | 0.25 |
| 2 | 530.9 | 24.8 | 284.6 | 61.5 | 398.4 | 12.1 | 0.20 |

1. silk/PEO fiber(80/20, wt/wt);
2. silk/PEO/poly-L-aspartic acid (200 mg poly-L-aspartic acid/g silk)

The N1s/C1s ratio of the silk mats without poly-L-aspartic acid was 0.25. After blending poly-L-aspartic acid, the N1s/C1s ratio decreased to 0.20, indicating that more PEO distributed near the fiber surface when the fibers contained poly-L-aspartic acid. FIG. 14 shows the highly resolved fitted C1s spectra and O1s spectra of the fiber mats with and without poly-L-aspartic acid. The analysis of the fitted XPS spectra allows characterization of the chemical environment of different elements. The carbon signal can be resolved into three different contributions: (1) hydrocarbon at about 285.0 eV, (2) ether carbon (O—C—O) from the PEO and amine (C—N) at about 286.6 eV, and (3) amide (N—C=O) from protein at about 288.3 eV. The intensity of ether and amine components is 57.8% of the total C1s intensity with poly-L-aspartic acid blending compared to 47.0% without blending. Two components can be fitted to the O1s spectra: (1) amide (N—C=O) at about 531.5 eV and (2) ether (C—O—C) from PEO and C—OH from protein at about 532.8 eV. The intensity of the component at 532.8 eV increased from 31.2% to 47.8% with poly-L-aspartic acid blending. The increase of ether component intensity also suggested that more PEO was distributed near the fiber surface with poly-L-aspartic acid blending.

Electrospinning of a polymer solution involves rapid solvent evaporation in the millisecond time scale[58,59]. This time frame may not allow the phase-separated regions to coarsen prior to solidification, resulting in a fine phase morphology. In addition, the elongation effect of the electrospinning process leads to the orientation of polymer molecules along the fiber axis[60,61]. Since PEO is water soluble, removal of the PEO revealed the internal structural of the fibers. A cross-section of a silk/PEO (80/20 wt/wt) blend fiber without poly-L-aspartic acid after PEO extraction in water for 48 hours reveals holes in the fiber reflective of the prior location of PEO prior to extraction. Therefore, the fibers have a morphology with a PEO phase inter-dispersed within the silk phase as irregular shapes, or the fiber has a cocontinuous morphology with PEO inter-dispersed within the silk phase as continuous strands. The fibers had a cocontinuous morphology when poly-L-aspartic acid was included.

III. Apatite Deposition on Fiber Mats

Apatite has been used in orthopedic and dental surgery due to its biocompatibility and osteoconductivity. Apatite contributes to the formation of strong bonds in bone as well as to early bone formation around implants[62,63]. The partial dissolution of apatite causes an increase in supersaturation level of hydroxyapatite in the immediate microenvironment of an implant. Also, apatite can act heterogeneously and nucleate additional growth of apatite[64]. Recently, a novel apatite formation process was developed to generate large amounts of apatite in a relatively short time[28,57,65]. Using this process, coatings of hydroxyapatite on substrates were attained in hours instead of days using soaking in simulated body fluid (SBF) or 1.5×SBF[34,35].

Scattered (nonaligned) apatite particles were deposited on the electrospun silk fibroin fibers in the absence of blended poly-L-aspartic acid. In contrast, aligned growth of apatite along fiber axes was obtained when the poly-L-aspartic acid concentration was increased to 200 mg/g silk. Randomly oriented apatite particles formed on silk fibers at low concentrations of poly-L-aspartic acid. Therefore, the presence of polyaspartic acid on the silk fibers enhanced control of the deposition of apatite, reflecting the increased density and localization of the acid groups on the aligned silk templates. Human bone is composed of inorganic hydroxyapatite nanocrystals (50 nm×25 nm×2 nm) integrated with collagen fibers. The crystallographic c axis of the hydroxyapatite is preferentially parallel to the longitudinal direction of the collagen fibers[66]. Noncollageous proteins, such as osteonectin and phosphoproteins, are known to bind to collagen, possibly at particular sites as hole zones. These hole zones are considered potential sites for the specific nucleation and growth of hydroxyapatite crystals that are organized in bands across collagen fibers[67]. Previously, in vitro aligned growth of hydroxyapatite was obtained by using reconstituted collagen and self assembled peptide-amphiphile nanofibers as scaffolds[68-70]. Deposition of apatite on raw silk or degummed raw silk has been studied[57,71] and no aligned growth of hydroxyapatite along silk fiber has been previously reported. In this study, poly-L-aspartic acid, as an analogue of noncollageous proteins, was incorporated into electrospun silk fibers and induced the aligned growth of hydroxyapatite along the silk fibroin fiber axes.

The microstructure of the electrospun silk fibers with blended poly-L-aspartic acid was considered for the formation of aligned growth of apatite. The silk fibers electrospun from silk/PEO (80/20, wt/wt) displayed microphase separation between the silk fibroin and PEO. At high poly-L-aspartic acid concentration, phase separation was more evident visually prior to electrospinning, since the silk/PEO solution turned turbid after addition of the poly-L-aspartic acid. Further phase separation during the electrospinning process would lead to a cocontinuous structure with regular silk and PEO strands oriented along the fiber axis. The silk fibers showed grooves along the fiber axes after soaking in 120 mM $CaCl_2$ solution for 2 hours, which may be partially due to the dissolution of PEO phase.

Carboxyl groups enhance apatite deposition on polymer substrates[23,24,33]. The formation of apatite on negatively charged surfaces can initiate from complexation with calcium ions, followed by nucleation and crystal growth. Once soaked in $CaCl_2$ solution, the calcium ions can coordinate with the carboxyl groups and complexes such as —$COOCa^+$ and (—COO)$_2$Ca form. Furthermore, bridges between silk molecules and poly-L-aspartic acid molecules can form to generate a gel-like structure along the silk bands. Ca ions can facilitate the gelation of silk/poly-L-aspartic acid system (unpublished data) as well as silik fibroin alone[72]. Therefore, the aligned growth of the apatite can be obtained by heterogeneous nucleation of apatite on the silk-rich bands with the coordination of acidic groups from the poly-L-aspartic acid. In the case of silk fibers without poly-L-aspartic acid, the amount of apatite deposited was lower. Silk fibroin contains hydrophilic polar groups, 16.5 mol % hydroxyl and 2.9 mol % carboxyl residues, which would facilitate the nucleation of apatite through the formation of ion-ion (between $Ca^{2+}$ and carboxyl group) and ion-polar (between $Ca^{2+}$ and hydroxyl and carbonyl groups) interactions.

In a control experiment, poly-L-lysine was incorporated into electrospun silk fibers and studied for mineralization response in a similar fashion to that described for the polyaspartic acid system. No mineral deposited when the electrospun silk mat was soaked in the calcium solution first, and only small amounts of mineral formed when the fibers were soaked in the phorphorous solution first. The positively charged poly-L-lysine containing fiber surface did not facilitate the binding of Ca ions. Although a complex structure might form between phosphate ions and surface amino groups via electrostatic interaction, there is insufficient subsequent complexation of $Ca^{2+}$ with the preformed phosphate-amino complex. Negatively charged surfaces (poly-L-aspartic acid) had more potential to induce the nucleation of hydroxyapatite, consistent with results of previous studies[23]. Another factor that may affect the HA nucleation is the high surface area of the electrospun fiber mat. The porous structure of the fiber mat could retain more Ca or phosphate solution, which could be released to the mineralization media. This explanation doesn't exclude the possibility that apatite could nucleate homogeneously in solution and subsequently deposit on the fiber surface.

Soaking time and cycles on the polyaspartic acid containing fibers affect mineral deposition. Elemental analysis of the materials after mineralization was performed with EDS. The main elements of the mineralized silk mat were carbon, oxygen, calcium and phosphorus. Small amounts of sodium and chlorine also were present. The carbon and oxygen could be from both silk and deposited minerals, while calcium and phosphorus could only be from deposited minerals. With the increase of soaking time and number of cycles, the amount of deposited minerals increased. For example, with 200 mg poly-L-asp/g silk fiber had a nitrogen peak attributed to the composition of silk that was not detected by EDS analysis after 3 cycles of 10-min soaking of the fibers (FIG. 15). XPS analysis of the same sample did not show a N1s peak, which also indicated that silk fibers were fully coated with apatite after 3 cycles of 10-minute soaking (data not shown). The Ca/P ratio of the hydroxyapatite was 1.67, with the chemical formula $Ca_{10}(PO_4)_6(OH)_2$. The typical Ca/P ratio of the apatite formed in this study by EDS analysis (Table 2) was much smaller than the stoichiometric Ca/P value of hydroxyapatite. In comparison, the Ca/P ratio of hydroxyapatite was about $1.61\pm0.02$ by the same technique, which is close to the Ca/P value of $1.664\pm0.005$ provided by NIST for standard hydroxyapatite.

TABLE 2

Ca/P molar ratio of apatite deposited on silk mats

| Sample | Ca/P |
|---|---|
| no poly-L-asp, 10 minutes, 3 cycles | 1.345 ± 0.02 |
| no poly-L-asp, 10 minutes, 3 cycles | 1.349 ± 0.01 |
| 200 mg poly-L-asp/g silk, 10 min, 3 cycles | 1.334 ± 0.03 |
| 200 mg poly-L-asp/g silk, 10 min, 3 cycles | 1.374 ± 0.04 |

Some sites for the $PO_4^{3-}$ could be substituted by $HPO_4^{2-}$ and $CO_3^{2-}$. Since $CO_3^{2-}$ ions were not included in the alternate soaking process, the substitution with $CO_3^{2-}$ should be very low. Theoretically, the substitution of one $HPO_4^{2-}$ for $PO_4^{3-}$ results in a half Ca deficiency, which will result in a Ca/P ratio less than 1.67. To maintain the charge balance, Na ions can substitute for Ca ions. EDS analysis detected considerable amounts of Na for all the samples, which could be partially due to the incorporation of Na ions into the apatite lattice or the amorphous phase.

XRD patterns of the mineralized silk fibers showed that the deposited minerals were hydroxyapatite (FIG. 16). With increased soaking times and number of cycles, XRD diffraction peaks became sharper, indicating higher crystallinity. Comparing the XRD patterns with the hydroxyapatite standard, the major peaks (002, 211) match. However, the diffraction reflections appeared broadened with respect to those recorded from the hydroxyapatite standard. The peak broadening indicated poor crystallinity, which could be caused by disorder in the crystal, such as the substitution of $HPO_4^{2-}$ for $PO_4^{3-}$ or Na for ions Ca ions. These results are consistent with the fact that the amorphous calcium phosphate precursor gradually converts into stable hydroxyapatite when apatite forms in aqueous solution. Poorly crystallized apatite layer tends to be covered with non-apatitic highly reactive labile ions of $CO_3^{2-}$, $PO_4^{3-}$, $HPO_4^{2-}$, which can modulate the adsorption of adhesion ligands to facilitate cell attachment[73]. These properties are not expected from highly crystalline apatite[74].

The present work shows that the cooperation of silk template and acidic peptides can provide the molecular design necessary for controlling the nucleation and growth of apatite. Control of nucleation and growth of apatite can be accomplished on silk structures with 1D (fiber), 2D (film) and 3D (scaffold) features. By controlling the incorporation of acidic proteins into these structures, hence controlling the location of the nucleation site, silk composites in various forms can be obtained.

IV. Conclusion

Non-woven electrospun silk fibroin fibers were prepared and used as matrices for controlled apatite deposition to form nanaocomposites. Aligned growth of polycrystalline apatite along the longitudinal axis of the fibers was obtained when the fibers were functionalized with poly-L-aspartic. As an analogue of noncollageous protein in natural bone, poly-L-aspartic acid rich in carboxylate groups resulted in enhanced control of growth of apatite. The results suggest new directions in the design and fabrication of controlled molecular composites with relevance to bone substitutes because of the excellent bone-binding property of apatite.

All references described herein are incorporated herein by reference.

REFERENCES

[1]. Weiner, S.; Traub, W. *Phil. Trans. R. Soc. Lond. B.* 1984, 304, 425-434

[2]. Nakahara, H. In *Biomineralization and Biological Metal Accumulation*, Westbroek, P.; de Jong, E. W., Eds.; Reidel, Dordrecht, 1983, pp. 225-230

[3]. Mann S. In *Biomineralization Principles and Concepts in Biogenic Materials* Compton R. G., Davies, S. G., Evans J., Eds.; Chemistry Oxford University Press: New York, 2001; Chapter 6, pp. 92

[4]. Kaplan, D. L.; Mello, C. M.; Arcidiacono, S.; Fossey, S.; Senecal, K.; Muller, W. Silk. In *Protein-Based Materials*, McGrath K., Kaplan D., Eds.; Birkhauser, Boston, Mass., 1997; pp. 103-131

[5]. Mori, H.; Tsukada, M. New silk protein: modification of silk protein by gene engineering for production of biomaterials *Reviews in Molecular Biotechnology* 2000, 74, 95-103

[6]. Jin, H-Y; Fridrikh, S. V.; Rutledge G. C.; Kaplan D. L. *Biomacromolecules*, 2002, 3, 1233-1239

[7]. Addadi, L.; Moradian, J.; Shay E.; Maroudas N. G.; Weiner, S. *Proc. Natl. Acad. Sci. USA* 1987, 84, 2732-2736

[8]. Wierzbicki, A.; Sikes, C. S.; Madura, J. D.; Drake, B. *Calcified Tissue International*. 1994, 54, 133-141

[9]. Mann, S.; Didymus, J. M.; Sanderson, N. P.; Heywood, B. R.; Samper, E. J. A. *Journal of Chemical Society, Faraday Transction* 1990, 86, 1873-1880

[10]. Alberk, S.; Aizenberg, J.; Addadi, L; Weiner, S.; *Journal of the American Chemical Society* 1993, 115, 11691-11697

[11]. DeOliveira, D. B.; Laursen, R. A. Journal of American Chemical Society 1997, 119, 10627

[12]. Falini, G.; Ferma K., mani, S.; Gazzano, M; Ripamonti, A. *Journal of Chemical Society, Dalton Transactions* 2000, 3983-3987.

[13]. Falini, G. *International Journal of Inorganic Materials* 2000, 2, 455-461

[14]. Falini, G.; Fermani, S.; Gazzano, M.; Ripamonti, A. *Chemistry, A European Journal* 1998, 4, 1048-1052

[15]. Falini, G.; Fermani, S.; Gazzano, M.; Ripamonti, A. *Chemistry, A European Journal* 1997, 3, 1807-1814

[16]. Falini, G.; Gazzano, M.; Ripamonti, A. *Advanced Materials* 1994, 6, 46-48
[17]. Chou, P. Y.; Fsaman, G. D. *Biochemistry* 1974, 13, 222-245
[18]. Alder, A. J.; Hoving R.; Potter, J.; Wells, M.; Fasman, G. D. *J. Am. Chem. Soc.* 1968, 90, 4736
[19]. Shao, Z; Young, R. J.; Vollrath, F. *International Journal of Biological Macromolecules* 1999, 24, 295-300
[20]. Furuzono, T., Taguchi, T., Akashi, M., Tamada, Y. *J. Biomed. Mater. Res.* 2000; 50, 344-352
[21]. Taguchi, T., Muraoka, Y., Matsuyama, H., Kishida, A., Akashi, M. *Bioimaterials* 2001; 22, 53-58.
[22]. Li, C. & Kaplan, D. L., *Current opinion in solid state & materials science* 7, 265-271 (2003).
[23]. Sato, K., Kumagai, Y. & Tanaka, J., *Journal of biomedical materials research* 50, 16-20 (2000).
[24]. Tanahashi, M. & Matsuda, T., *Journal of biomedical materials research* 34, 305-315 (1997).
[25]. Kamei, S., Tomita, N., Tamai, S., Kato, K. & Ikada, Y., *Journal of biomedical materials research* 37, 384-393 (1997).
[26]. Kato, K., Eika, Y. & Ikada, Y., *Journal of biomedical materials research* 32, 687-691 (1996).
[27]. Tretinnikov, O., Kato, K. & Ikada, Y., *Journal of biomedical materials research* 28, 1365-1373 (1994).
[28]. Taguchi, T., Muraoka, Y., Matsuyama, H., Kishida, A. & Akashi, M., *Biomaterials* 22, 53-58 (2001).
[29]. Tanahashi, M. et al., *Journal of Applied Biomaterials* 5, 339-347 (1994).
[30]. Tanahashi, M. et al., *Journal of biomedical materials research* 29, 349-357 (1995).
[31]. Kawai, T. et al., *Biomaterials* 25, 4529-4534 (2004).
[32]. Wan, A. C. A., Khor, E. & Hastings, G. W., *Journal of biomedical materials research* 41, 541-548 (1998).
[33]. Kawashita, M. et al., *Biomaterials* 24, 2477-2484 (2003).
[34]. Bigi, A., Boanini, E., Panzavolta, S., Roveri, N. & Rubini, K., *Journal of biomedical materials research* 59, 709-714 (2002).
[35]. Zhang, R. & Ma, P. X., *Journal of biomedical materials research* 45, 285-293 (1999).
[36]. Murphy, W. L., Kohn, D. H. & Mooney, D. J., *Journal of biomedical materials research* 50, 50-58 (2000).
[37]. Oyane, A. et al., *Biomaterials* 24, 1729-1735 (2003).
[38]. Altman, G. H. et al., *Biomaterials* 24, 401-416 (2003).
[39]. Panilaitis, B. et al., *Biomaterials* 24, 3079-3085 (2003).
[40]. Altman, G. H. et al., *Biomaterials* 23, 4131-4141 (2002).
[41]. Chen, J. et al., *Journal of biomedical materials research in press* (2003).
[42]. Yoshimoto, H., Shin, Y. M., Terai, H. & Vacanti, J. P., *Biomaterials* 24, 2077-2082 (2003).
[43]. Kenawy, E.-R. et al., *Journal of Controlled Release* 81, 57-64 (2002).
[44]. Stitzel, J. D., Pawlowski, K., Wnek, G. E., Simpson, D. G. & Bowlin, G. L., *Journal of biomaterials applications* 15, 1-13 (2001).
[45]. Matthews, J. A., Wnek, G. E., Simpson, D. G. & Bowlin, G. L., *Biomacromolecules* 3, 232-238 (2002).
[46]. Jin, H.-J., Chen, J., Karageorgiou, V., Altman, G. H. & Kaplan, D. L., *Biomaterials* 25, 1039-1047 (2004).
[47]. Huang, L. et al., *Macromolecules* 33, 2989-2997 (2000).
[48]. Anderson, J. P. N., S. C.; Rajachar, R. M.; Logan, R.; Weissman, N. A.; Martin, D. C., *Biomolecular materials by design* (ed. Alper, M. B., H., Kaplan, D., Navia, M.) (Materials Research Society, Pittsburgh, Pa., 1994).
[49]. Buchko, C. J., Chen, L. C., Shen, Y. & Martin, D. C., *Polymer* 40, 7397-7407 (1999).
[50]. Buchko, C. J., Kozloff, K. M. & Martin, D. C., *Biomaterials* 22, 1289-1300 (2001).
[51]. Jin, H.-J., Fridrikh, S. V., Rutledge, G. C. & Kaplan, D. L., *Biomacromolecules* 3, 1233-1239 (2002).
[52]. Huang, L., Nagapudi, K., Apkarian, R. P. & Chaikof, E. L., *Journal of Biomaterials Science, Polymer Edition* 12, 979-993 (2001).
[53]. Huang, L., Apkarian, R. P. & Chaikof, E. L., *Scanning* 23, 372-375 (2001).
[54]. Zarkoob, S. et al., *Polymer Preprints (American Chemical Society, Division of Polymer Chemistry)* 39, 244-245 (1998).
[55]. Bini, E., Knight, D. P. & Kaplan, D. L., et al. *Journal of Molecular Biology* 335, 27-40 (2004).
[56]. Jin, H.-J. & Kaplan, D. L., et al. *Nature* 424, 1057-1061 (2003).
[57]. Furuzono, T., Taguchi, T., Kishida, A., Akashi, M. & Tamada, Y., *Journal of biomedical materials research* 50, 344-352 (2000).
[58]. Bognitzki, M., Frese, T., Steinhart, M., Greiner, A. & Wendorff, H., *Polymer science and engineering* 41, 982-989 (2001).
[59]. Fong, H. & Reneker, D. H., *J Polym Sci B: Polym Phys* 37, 3488-3493 (1999).
[60]. Chen, Z., Foster, M. D., Zhou, W., Fong, H. & Reneker, D. H., *Macromolecules* 34, 6156-6158 (2001).
[61]. Jaeger, R., Schönherr, H. & Vancso, G. J., *Macromolecules* 29, 7634-7636 (1996).
[62]. Hench, L., *Journal of American Ceramics Society* 74, 1487-1510 (1991).
[63]. Kokubo, T., *Journal of Ceramics Society Japan* 99, 965-973 (1991).
[64]. Daculsi, G., LeGeros, R. Z., Heughebaert, M. and Barbieux, I., *Calcified Tissue International* 46, 20-27 (1990).
[65]. Taguchi, T., Kishida, A. & Akashi, M., *Chemistry Letters* 8, 711-712 (1998).
[66]. Sasaki, N. & Sudoh, Y., *Calcif Tissue Int* 60, 361-367 (1997).
[67]. Weiner, S. & Traub, W., *FEBS Letters* 206, 262-266 (1986).
[68]. Kikuchi, M., Itoh, S., Ichinose, S., Shinomiya, K. & Tanaka, J., *Biomaterials* 22, 1705-1711 (2001).
[69]. Rhee, S.-H., Suetsugu, Y. & Tanaka, J., *Biomaterials* 22, 2843-2847 (2001).
[70]. Roveri, N. et al., *Materials Science and Engineering: C* 23, 441-446 (2003).
[71]. Takeuchi, A. et al., *Journal of biomedical materials research* 65A, 283-289 (2003).
[72]. Kim, U.-J. et al., *Biomacromolecules* 5, 786-792 (2004).
[73]. Kim, H.-M. et al., *Biomaterials* 21, 1129-1134 (2000).
[74]. Frayssinet, P., Trouillet, J. L., Rouquet, N., Azimus, E. & Autefage, A., *Biomaterials* 14, 423-429 (1993).

We claim:
1. A matrix comprising
an aligned inorganic coating on a protein template comprising silk fibroin,
wherein the protein template further comprises an anionic polymer,
wherein the anionic polymer interacts with the protein template so that a surface is established that promotes nucleation and growth of inorganic crystals, wherein the anionic polymer comprises poly-L-aspartic acid and the aligned inorganic layer comprises hydroxyapatite, and wherein the weight ratio of the poly-L-aspartic acid to the silk fibroin is between 200 mg/g and 1 g/g, inclusive.

2. The matrix of claim 1, wherein the protein template further comprises at least one protein selected from keratins, collagens and silks.

3. The matrix of claim 1, further comprising at least one additive.

4. A silk fibroin template comprising
an aligned inorganic coating, and
at least one therapeutic or biologically active agent,
wherein the silk fibroin template comprises an anionic polymer,
wherein the anionic polymer interacts with the silk fibroin template and promotes more regular nucleation and growth of inorganic crystals,
wherein the anionic polymer comprises poly-L-aspartic acid and the aligned inorganic layer comprises hydroxyapatite, and
wherein the weight ratio of the poly-L-aspartic acid to the silk fibroin is between 200 mg/g and 1 g/g, inclusive.

5. The silk fibroin template of claim 4, wherein at least one therapeutic or biologically active agent is selected from the group consisting of: a small molecule, a protein, an antibody, a peptide, a nucleic acid, a polysaccharide, a glycoprotein, and a lipoprotein.

6. The silk fibroin template of claim 4, wherein the at least one therapeutic or biologically active agent is a biologically active agent selected from the group consisting of cell attachment mediators, biologically active ligands, enzymes, and substances that either promote or inhibit cellular tissue ingrowth.

7. The silk fibroin template of claim 4, wherein the at least one therapeutic or biologically active agent is a biologically active agent selected from the group consisting of collagen, elastin, fibronectin, vitronectin, laminin, proteoglycans, Arg-Gly-Asp (RGD) peptides, bone morphogenic proteins, cytokines, growth factor inhibitors, epidermal growth factor, fibroblast growth factor, platelet-derived growth factor, insulin-like growth factor, and transforming growth factor.

8. The silk fibroin template of claim 4, wherein the at least one therapeutic or biologically active agent is incorporated in, or coated on, the aligned inorganic coating.

9. The silk fibroin template of claim 4, wherein the at least one therapeutic or biologically active agent is incorporated in, or coated on, the silk fibroin template.

10. The silk fibroin template of claim 4, wherein the silk fibroin template is selected from the group consisting of a silk fiber, a silk thread, a silk mesh, a silk film, a silk hydrogel, or a silk foam.

11. The silk fibroin template of claim 4, wherein the silk fibroin template is a three-dimensional porous silk matrix.

12. The silk fibroin template of claim 4, further comprising a pharmaceutically acceptable carrier.

13. The silk fibroin template of claim 4, wherein the at least one therapeutic agent or biologically active agent is a therapeutic agent selected from the group consisting of anti-infectives, chemotherapeutic agents, anti-rejection agents, analgesics and analgesic combinations, anti-inflammatory agents, hormones, anti-angiogenic agents, anti-thrombotics, anti-metabolics, antimitotics, anticoagulants, fibrinolytics, growth factor inhibitors, growth factors, vitamins, sedatives, hypnotics, antibiotics, antiviral agents, steroids, growth factor promoters, prostaglandins, and radiopharmaceuticals.

14. The silk fibroin template of claim 13, wherein the growth factor is selected from the group consisting of bone morphogenic proteins, bone morphogenic-like proteins, epidermal growth factor, fibroblast growth factor, platelet derived growth factor, insulin-like growth factor, transforming growth factors, and vascular endothelial growth factor.

* * * * *